US012029519B2

United States Patent
Fischer et al.

(10) Patent No.: US 12,029,519 B2
(45) Date of Patent: Jul. 9, 2024

(54) ARTICULATION CAPSTAN TENSION RETAINMENT USING CLUTCH MECHANISM

(71) Applicant: Cilag GmbH International, Zug (CH)

(72) Inventors: Austin Michael Fischer, Blue Ash, OH (US); William George Saulenas, Blue Ash, OH (US); Eric N. Johnson, Maineville, OH (US)

(73) Assignee: Cilag GmbH International, Zug (CH)

( * ) Notice: Subject to any disclaimer, the term of this patent is extended or adjusted under 35 U.S.C. 154(b) by 398 days.

(21) Appl. No.: 17/172,518

(22) Filed: Feb. 10, 2021

(65) Prior Publication Data
US 2022/0249184 A1 Aug. 11, 2022

(51) Int. Cl.
*A61B 34/30* (2016.01)
*A61B 34/00* (2016.01)

(52) U.S. Cl.
CPC ........ *A61B 34/71* (2016.02); *A61B 2034/715* (2016.02)

(58) Field of Classification Search
CPC ... A61B 34/71; A61B 2034/715; A61B 34/37; A61B 34/30; A61B 34/32; A61B 34/35; A61B 2034/301–306
See application file for complete search history.

(56) References Cited

U.S. PATENT DOCUMENTS

| | | | | |
|---|---|---|---|---|
| 2012/0071895 | A1* | 3/2012 | Stahler | A61B 34/20 606/130 |
| 2018/0079074 | A1* | 3/2018 | Devengenzo | G16H 40/63 |
| 2018/0104011 | A1* | 4/2018 | Kadokura | A61B 34/30 |
| 2018/0104012 | A1* | 4/2018 | Wixey | A61B 34/71 |
| 2018/0271608 | A1* | 9/2018 | Ragosta | F16H 55/17 |
| 2018/0318024 | A1* | 11/2018 | Yoshii | B25J 3/04 |
| 2019/0125464 | A1* | 5/2019 | Remm | A61B 17/29 |
| 2019/0125465 | A1* | 5/2019 | Evans | A61B 34/30 |
| 2019/0125468 | A1* | 5/2019 | Adams | A61B 34/30 |
| 2020/0315728 | A1* | 10/2020 | Johnson | A61B 34/37 |

* cited by examiner

*Primary Examiner* — Erich G Herbermann
(74) *Attorney, Agent, or Firm* — Vorys, Sater, Seymour and Pease LLP

(57) ABSTRACT

A surgical tool includes a drive housing having an elongate shaft extending therefrom and an end effector arranged at a distal end of the shaft, a drive input rotatably mounted to the drive housing and having an input shaft extending therefrom, and upper and lower capstans mounted to the input shaft. First and second drive cables are coupled to the upper and lower capstans, respectively, and extend to the end effector, and a clutch feature is arranged to mate the upper capstan to the lower capstan and is movable between an engaged position, where rotation of the input shaft in either angular direction correspondingly rotates the upper and lower capstans in the same angular direction, and a disengaged position, where the upper and lower capstans are rotatable independent of each other in at least one angular direction.

13 Claims, 16 Drawing Sheets

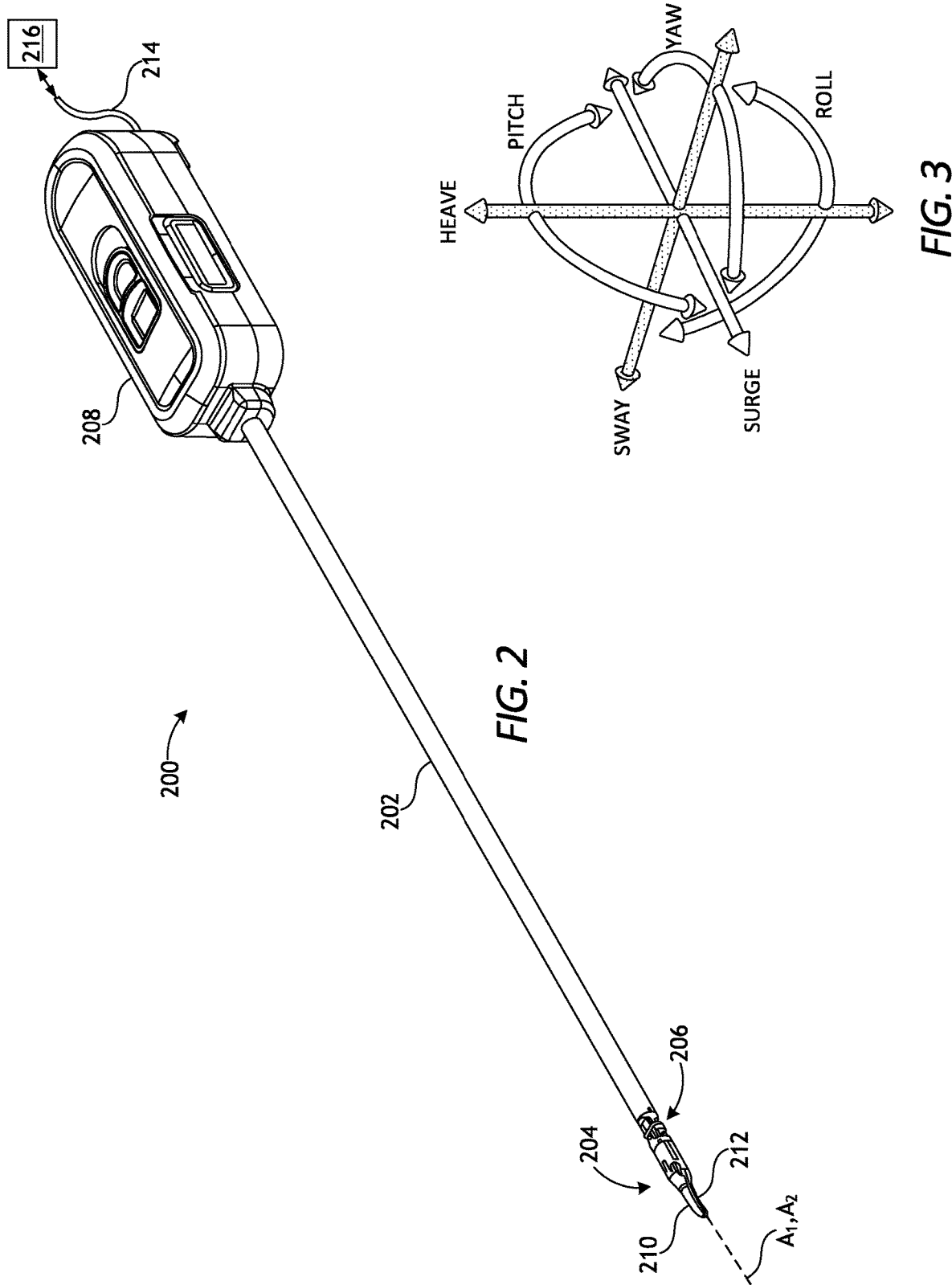

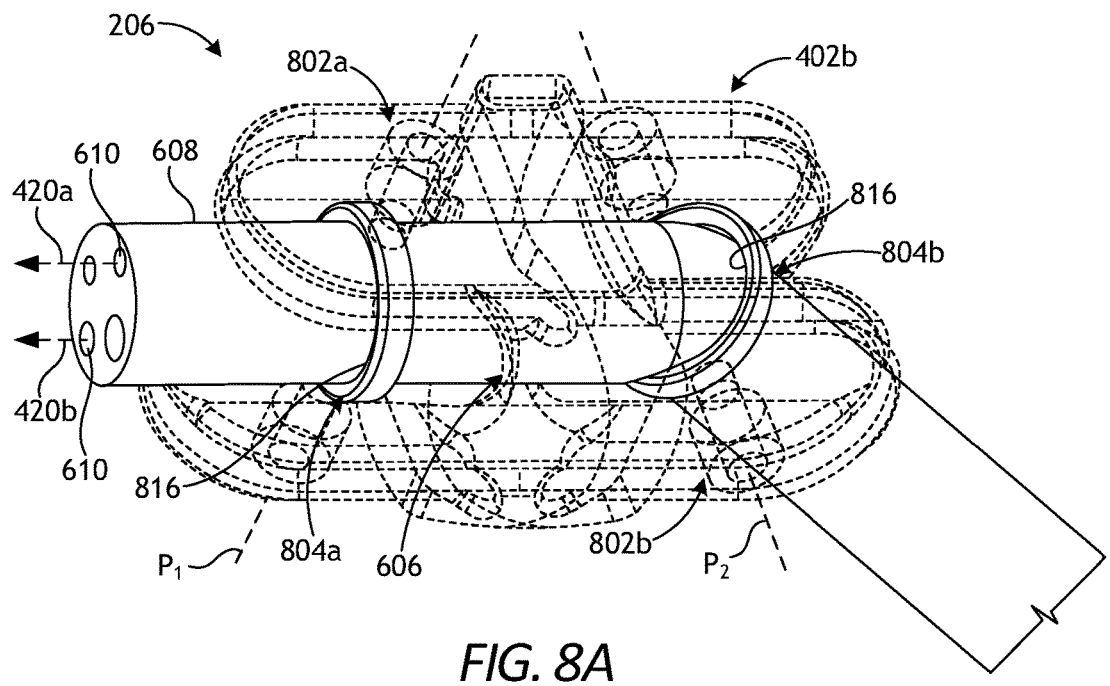
FIG. 8A
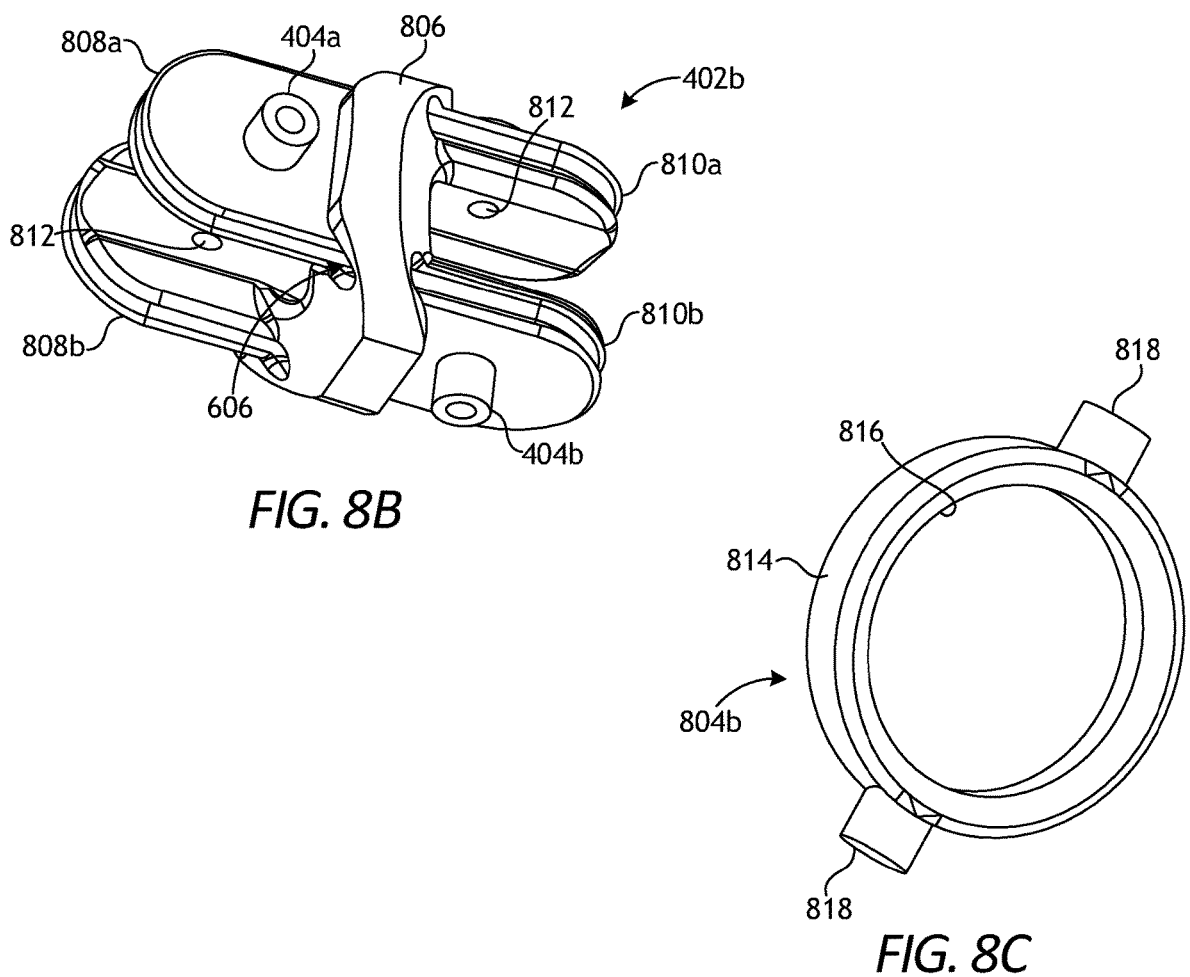
FIG. 8B
FIG. 8C

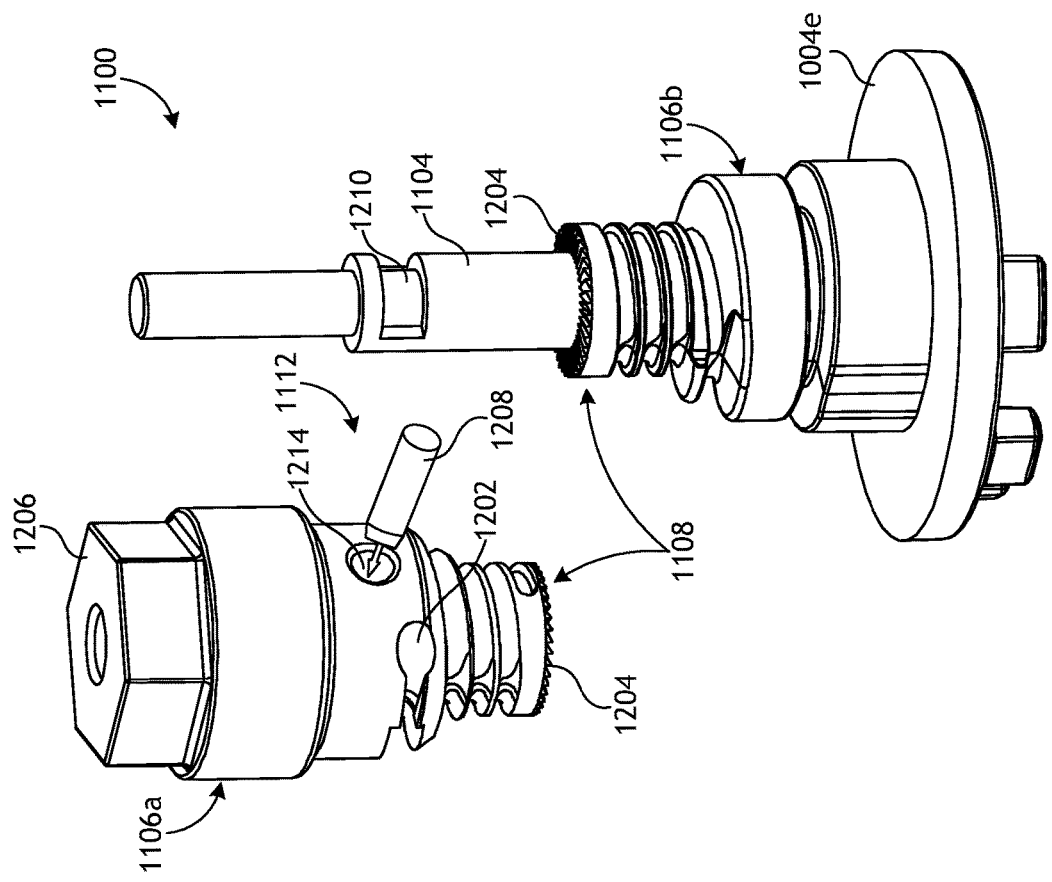
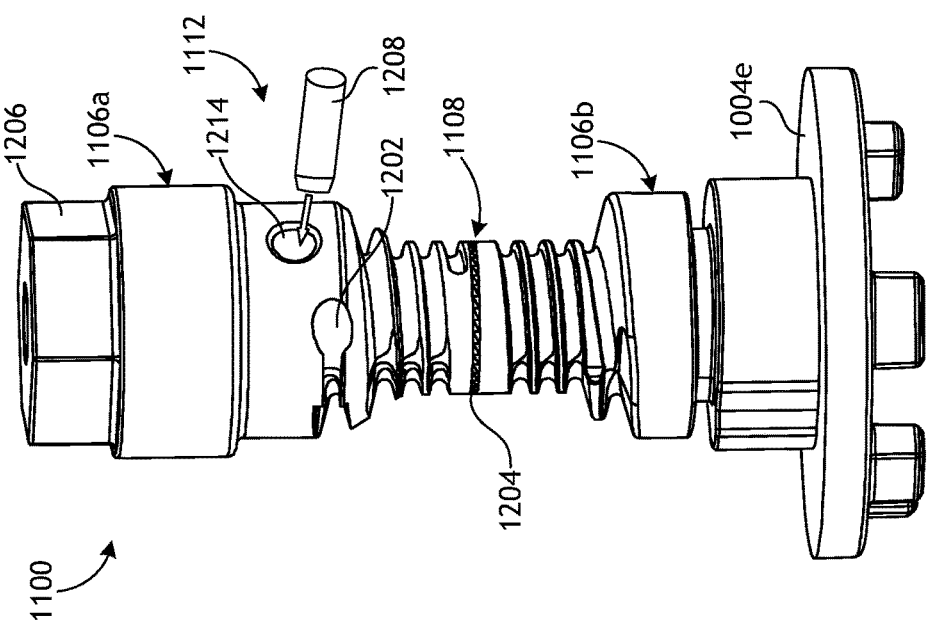
FIG. 12B
FIG. 12A

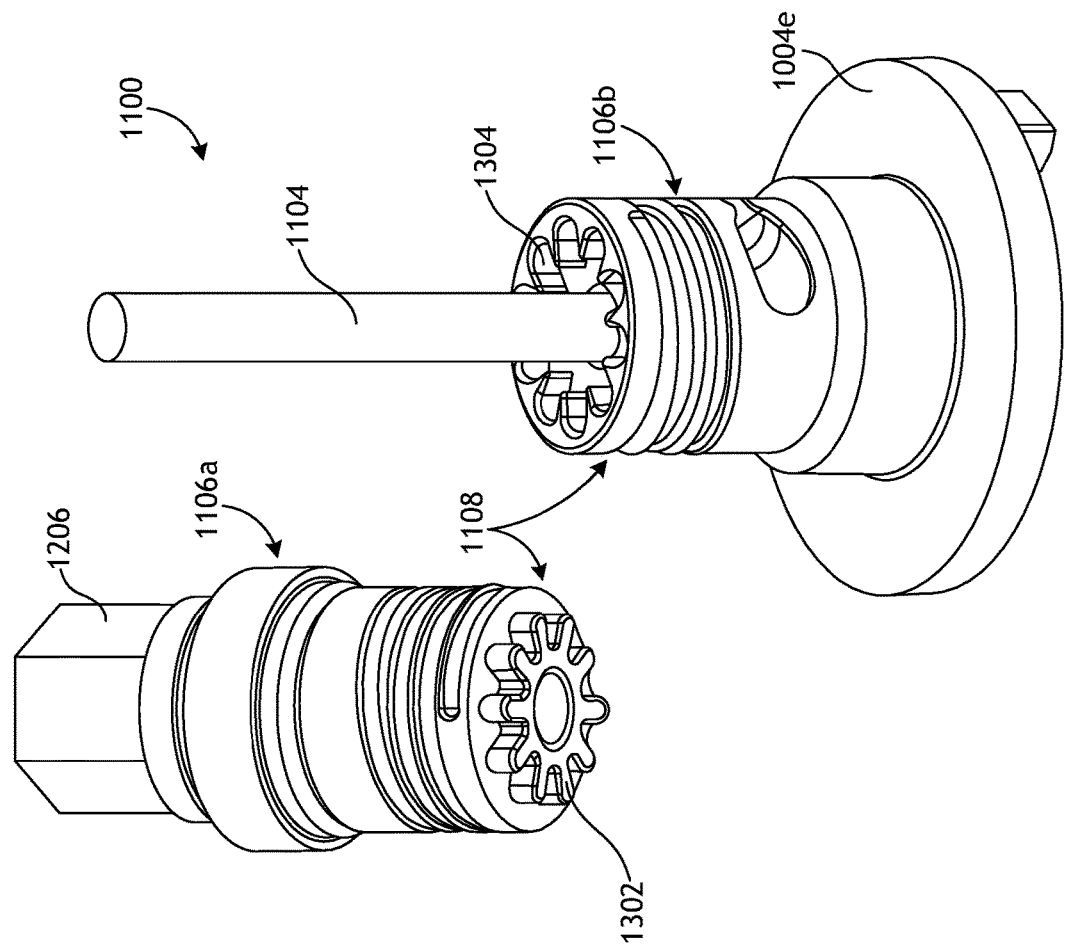
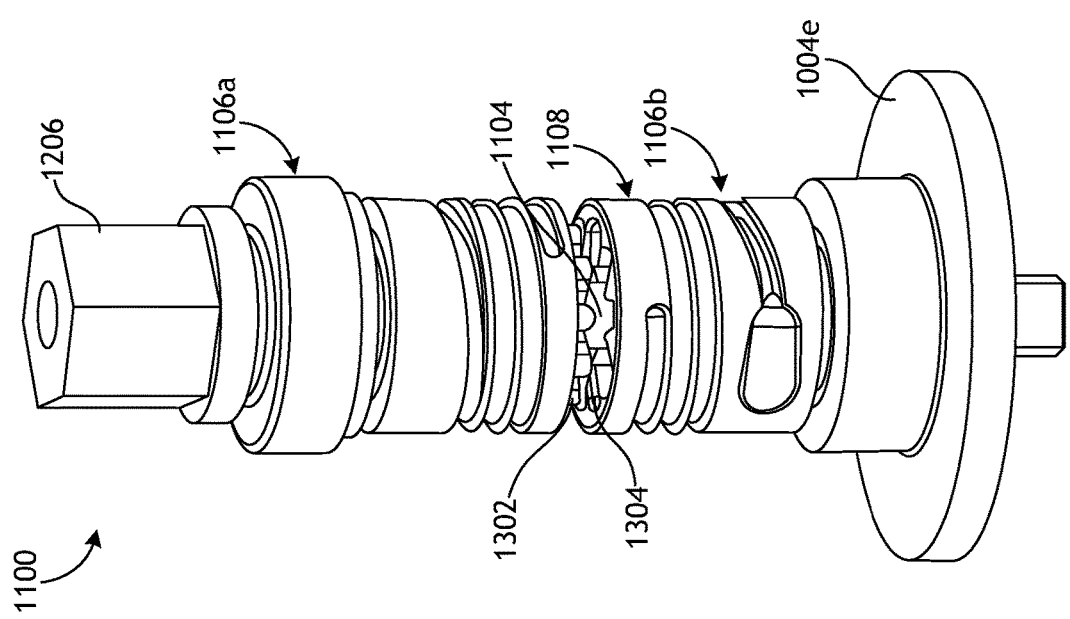
FIG. 13B
FIG. 13A

ARTICULATION CAPSTAN TENSION RETAINMENT USING CLUTCH MECHANISM

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

The drive cables extend from corresponding motor-driven capstans located within a drive housing of the robotic surgical tool. Before a robotic surgical tool is placed in service, the drive cables are often pre-tensioned to ensure proper response and operation. Current procedures for pre-tensioning drive cables utilize multiple manufacturing steps, and require the capstans to have a plastic overmold and costly metal inserts that help facilitate laser welding. What is needed is a system and method of pre-tensioning drive cables that allows tension in the cables to be initially set and retained over the course of the device life without the need for any welding.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

FIG. 8A is an isometric side view of another example embodiment of the wrist of FIGS. 4, 5, and 6A-6B that may incorporate one or more principles of the present disclosure.

FIG. 8B is an enlarged isometric view of an embodiment of the intermediate linkage of FIG. 8A.

FIG. 8C is enlarged isometric view of the second pivot guide of FIG. 8A.

FIGS. 12A and 12B are isometric assembled and exploded views of one example of the drive assembly of FIG. 11, according to one or more embodiments.

FIGS. 13A and 13B are isometric assembled and exploded views of another example of the drive assembly of FIG. 11, according to one or more embodiments.

DETAILED DESCRIPTION

The present disclosure is related to robotic surgical systems and, more particularly, to tensioning mechanisms for cable-based surgical instruments.

Figure 1:
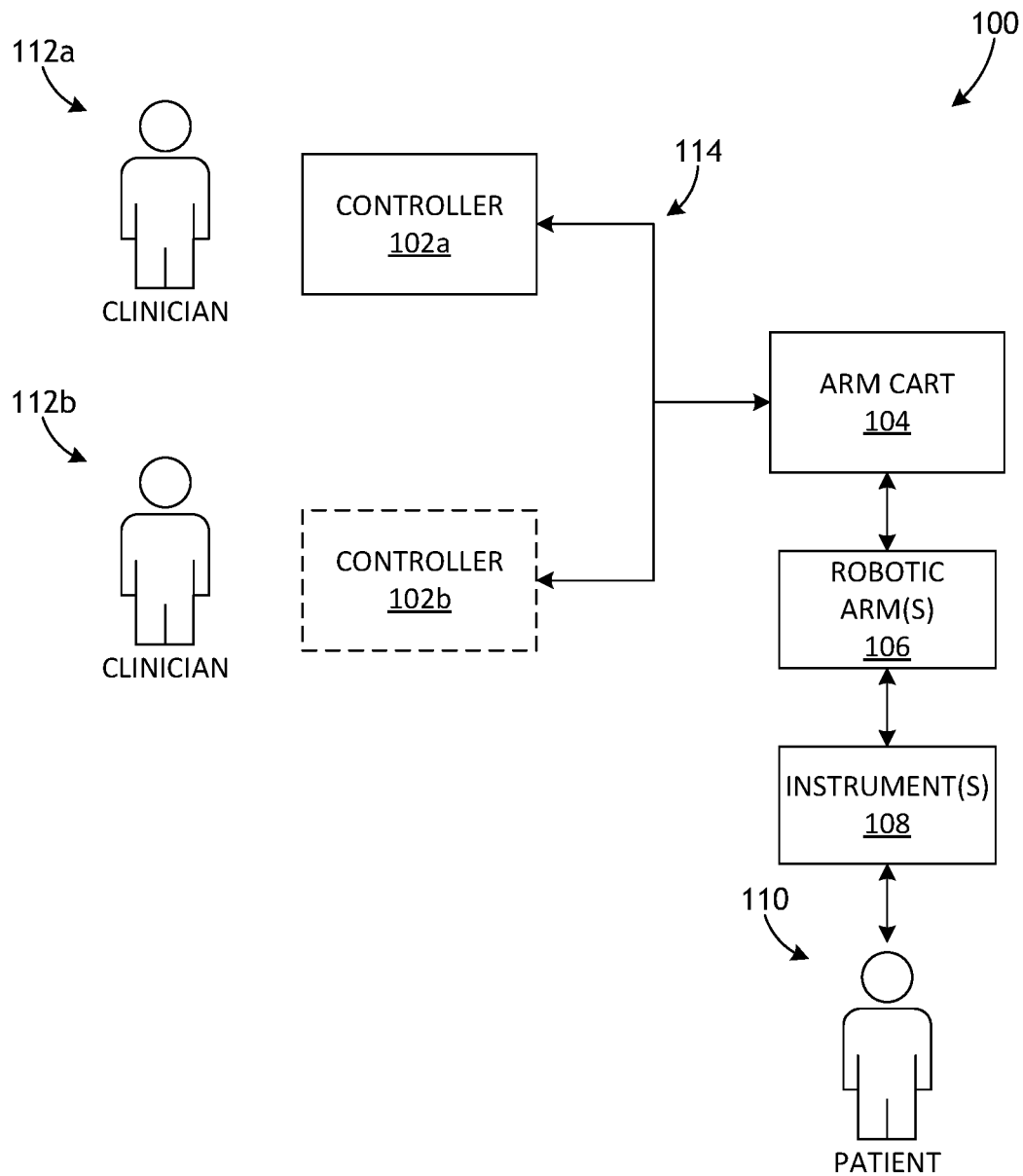
FIG. 1 is a block diagram of an example robotic surgical system that may incorporate some or all of the principles of the present disclosure.

One example surgical tool includes a drive housing with an elongate shaft extending therefrom and an end effector arranged at a distal end of the shaft. A drive input is rotatably mounted to the drive housing and an input shaft extends from the drive input. Upper and lower capstans may be mounted to the input shaft, and first and second drive cables may be coupled to the upper and lower capstans, respectively, and extend to the end effector. A clutch feature may be included in the surgical tool and arranged to mate the upper capstan to the lower capstan to help properly tension the drive cables. The clutch feature may be movable between an engaged position, where rotation of the input shaft in either angular direction rotates the upper and lower capstans in the same angular direction, and a disengaged position, where the upper and lower capstans are rotatable independent of each other in at least one angular direction to help place a tensile load on the drive cables. When the desired tension (torque) has been reached, the clutch feature may be transitioned to the engaged position, which operatively couples the upper and lower capstans for simultaneous rotation and operation FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally include one or more physical controllers that can be grasped by the clinician 112a,b and manipulated in space while viewing the procedure via a stereo display. The physical controllers generally comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some applications, the shaft 202, and hence the end effector 204 coupled thereto, is configured to rotate about a longitudinal axis $A_1$ of the shaft 202. In such embodiments, at least one of the drive inputs controls rotational movement of the shaft 202 about the longitudinal axis $A_1$.

The surgical tool 200 may include, but is not limited to, forceps, a grasper, a needle driver, scissors, an electrocautery tool, a vessel sealer, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy. In the illustrated embodiment, the end effector 204 comprises a combination tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

Figure 4:
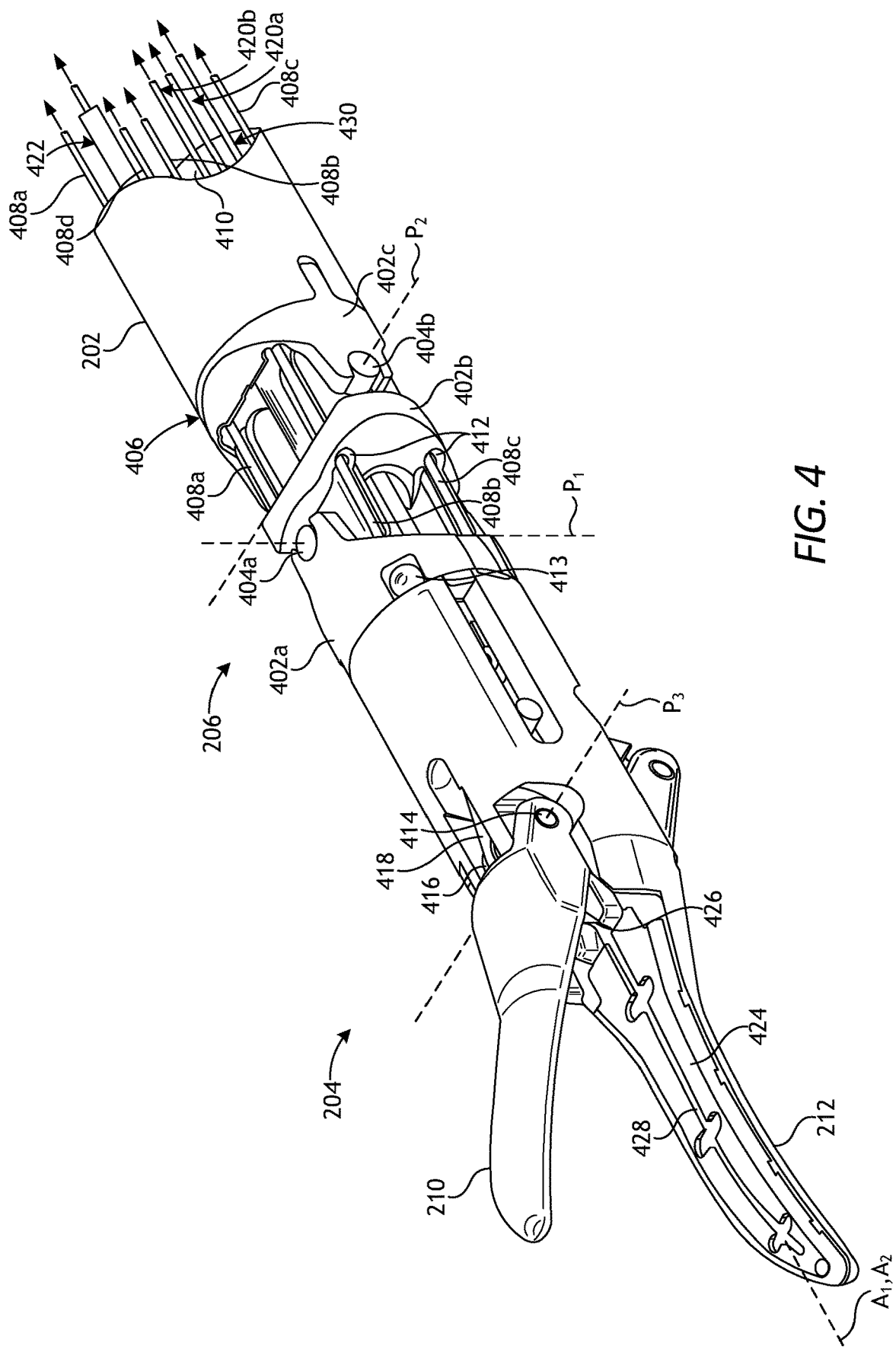
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c facilitate articulation of the end effector 204 relative to the elongate shaft 202. Articulation via the linkages 402a-c may be limited to pitch only, yaw only, or a combination of pitch and yaw. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

A first pivot axis $P_1$ extends through the first axle 404a and a second pivot axis $P_2$ extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (or a shaft adaptor) and pass through the wrist 206 to be operatively coupled to the end effector 204. The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of the drive cables 408a-d causes corresponding drive cables 408*a-d* to translate longitudinally within the lumen 410 and thereby cause pivoting movement (articulation) of the end effector 204. Moving a given drive cable 408*a-d* applies tension (i.e., pull force) to the given drive cable 408*a-d* in a proximal direction, which causes the given drive cable 408*a-d* to translate and thereby cause the end effector 204 to move (articulate).

The drive cables 408*a-d* each extend longitudinally through the first, second, and third linkages 402*a-c*. In some embodiments, each linkage 402*a-c* may define four, equidistantly-spaced apertures 412 (only two labeled) configured to guide the drive cables 408*a-d* through the wrist 206. The apertures 412 of each linkage 402*a-c* coaxially align when the end effector 204 is in the unarticulated position.

The distal end of each drive cable 408*a-d* may terminate at the distal linkage 402*a*, thus operatively coupling each drive cable 408*a-d* to the end effector 204 and, more particularly, to the lower jaw 212. The distal end of each drive cable 408*a-d* may be enlarged to facilitate fixed attachment thereof to the end effector 204. In some embodiments, as illustrated, the distal end of each drive cable 408*a-d* may include a ball crimp 413 (only one shown).

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$. In other embodiments, the end effector 204 may be designed such that the upper jaw 210 remains stationary as the lower jaw 212 pivots about the third pivot axis $P_3$, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408*a-d*, the jaw cable 418 extends longitudinally within the lumen 410 of the shaft 202 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420*a* and 420*b* of the jaw cable 418 extend proximally to the drive housing 208. Actuation of corresponding drive inputs will cooperatively cause tension or slack in the jaw cable 418 and thereby cause the upper jaw 210 to rotate about the third pivot axis $P_3$ between the open and closed positions. More specifically, a tensile load assumed on the first end 420*a* of the jaw cable 418 may operate to close the jaws 210, 212, and a tensile load assumed on the second end 420*b* of the jaw cable 418 may operate to open the jaws 210, 212. Consequently, the first end 420*a* of the jaw cable 418 may alternately be referred to as the "closure cable" and the second end 420*b* of the jaw cable 418 may alternately be referred to as the "open cable."

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In some embodiments, the electrical conductor 422 may comprise a wire, but may alternatively comprise a rigid or semi-rigid shaft, rod, or strip (ribbon) made of a conductive material. The electrical conductor 422 may be partially covered with an insulative covering (overmold) made of a non-conductive material. Using the electrical conductor 422 and the electrode 424, the end effector 204 may be configured for monopolar or bipolar operation.

In the illustrated embodiment, the end effector 204 comprises a combination tissue grasper and vessel sealer that includes a knife 426 (mostly occluded), alternately referred to as a "cutting element" or "blade." The knife 426 is aligned with and configured to traverse a guide track 428 defined longitudinally in one or both of the upper and lower jaws 210, 212. The knife 426 may be operatively coupled to the distal end of a drive rod 430 that extends longitudinally within the lumen 410 and passes through the wrist 206. Longitudinal movement (translation) of the drive rod 430 correspondingly moves the knife 426 within the guide track(s) 428. Similar to the drive and jaw cables 408*a-d*, 418, the drive rod 430 may form part of the cable driven motion system and, therefore, may extend proximally from the knife 426 to the drive housing 208 (FIG. 2). Selective actuation of a corresponding drive input will cause the drive rod 430 to move distally or proximally within the lumen 410, and correspondingly move the knife 426 in the same direction.

Figure 5:
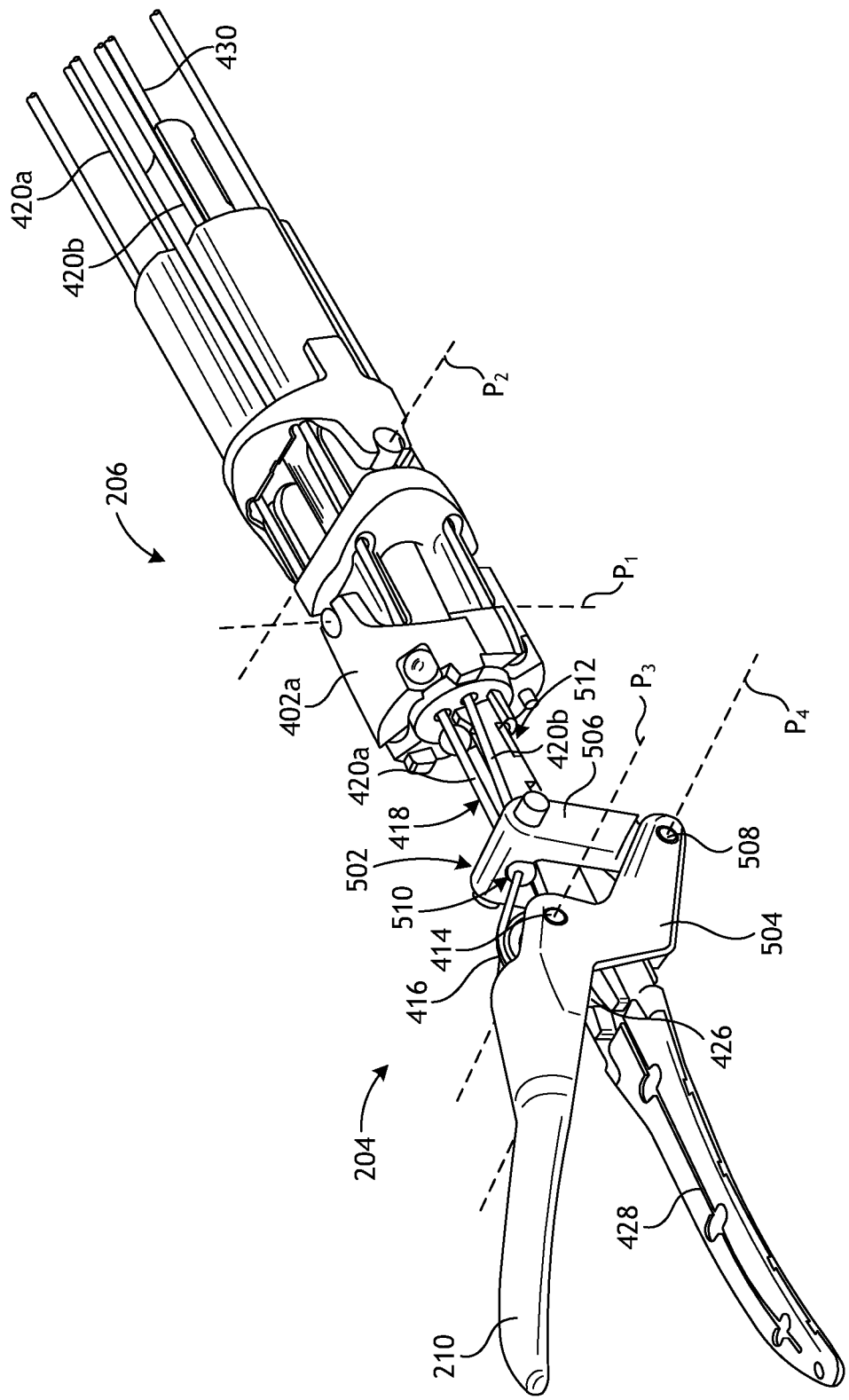
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and the opposing ends 420*a,b* of the jaw cable 418 extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420*a,b* of the jaw cable 418 and may help operatively couple the jaw cable 418 to the pivot link 502.

To move the jaws 210, 212 to the open position, the jaw cable 418 may be actuated to move the pivot link 502 distally, which may be done, for example, by pulling proximally on the second end 420*b* of the jaw cable 418 (i.e., the "open cable"). As the pivot link 502 moves distally, the legs 506 of the pivot link 502 act on the legs 504 of the upper jaw 210 at the pivot axle 508 and forces the legs 504 downward in rotation about the fourth pivot axis $P_4$. Downward movement of the legs 504 correspondingly causes the upper jaw 210 to pivot about the third pivot axis $P_3$. As it pivots about the third pivot axis $P_3$, the upper jaw 210 is moved to the open position.

To move the upper jaw 210 back to the closed position, the jaw cable 418 may be actuated to move the pivot link 502 proximally, which may be done by pulling proximally on the first end 420*a* of the jaw cable 418 (i.e., the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 to the closed position.

Figure 6A:
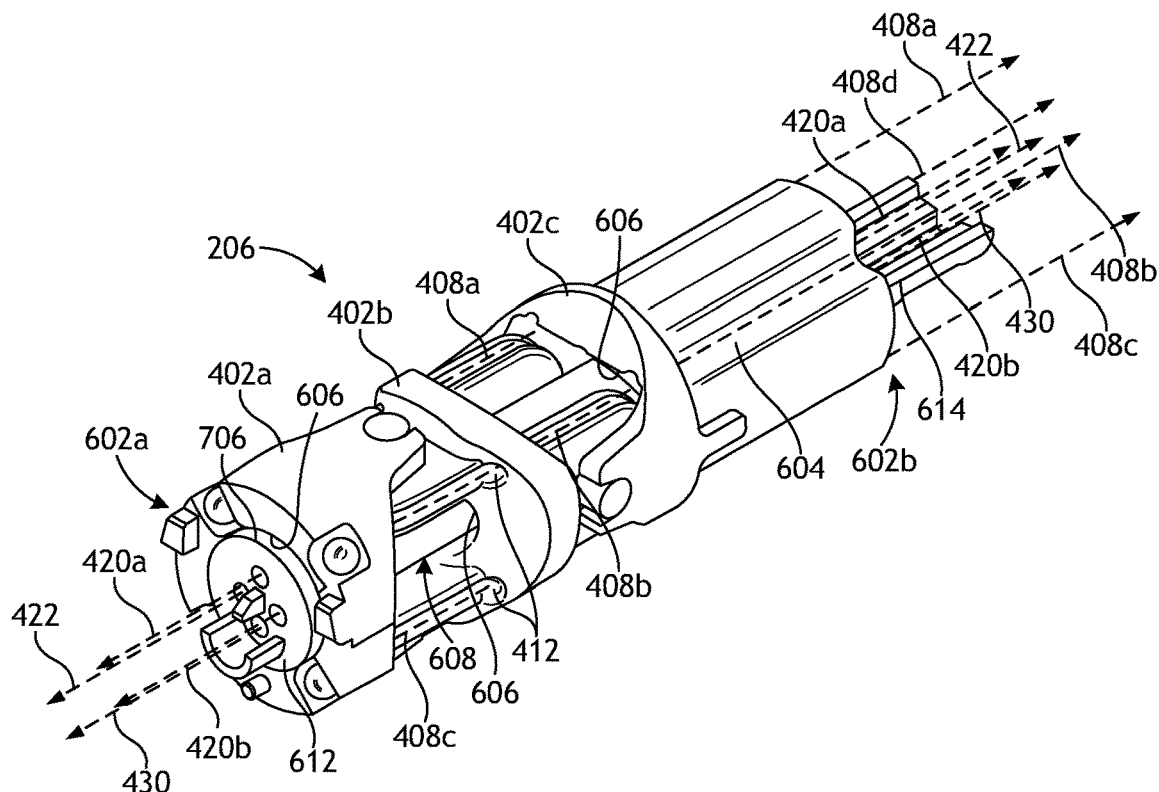
FIGS. 6A and 6B are enlarged isometric front and back views, respectively, of the wrist of FIGS. 4 and 5, according to one or more embodiments.
Figure 6B:
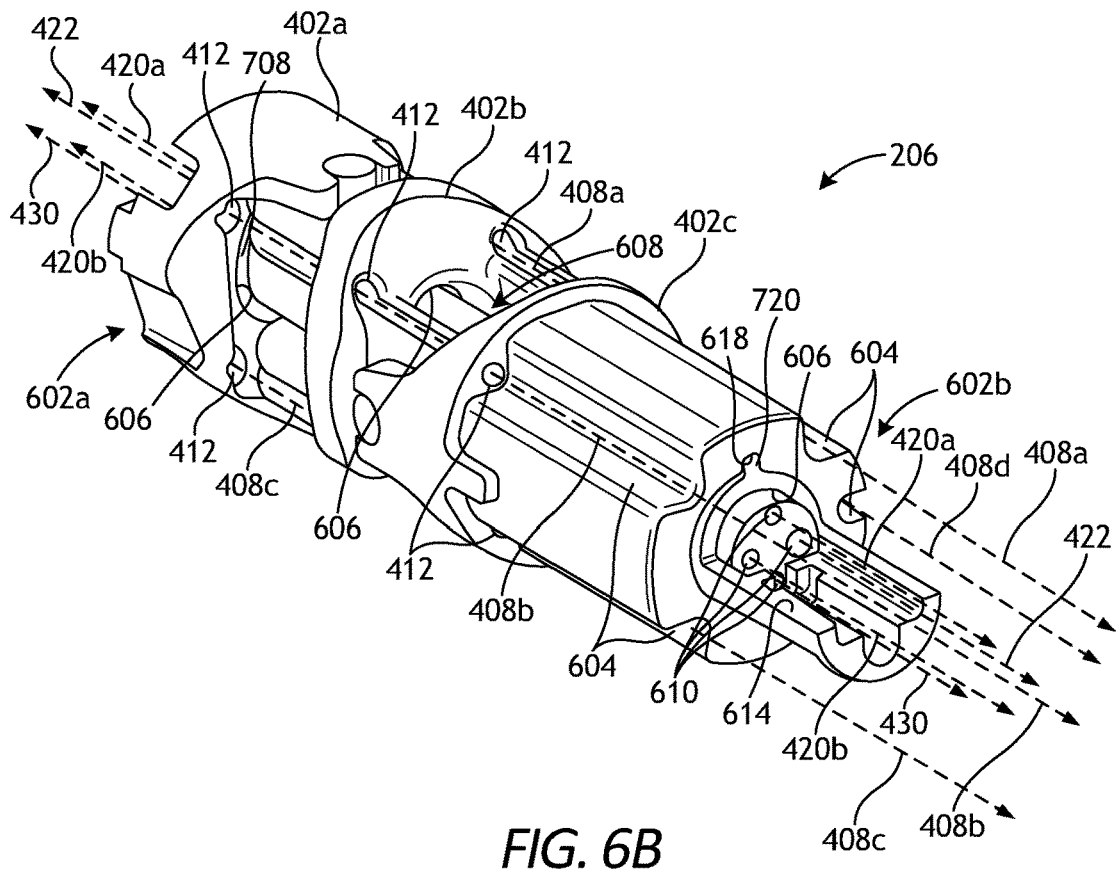

FIGS. 6A and 6B are enlarged isometric front and back views, respectively, of the wrist 206, according to one or more embodiments. The wrist 206 has a first or "distal" end 602a and a second or "proximal" end 602b opposite the distal end 602a. The distal linkage 402a is positioned at the distal end 602a, the proximal linkage 402c is positioned at the proximal end 602b, and the intermediate linkage 402b interposes and operatively couples the distal and proximal linkages 402a,c. However, embodiments are contemplated herein where the intermediate linkage 402b is omitted and the distal and proximal linkages 402a,c are alternatively directly coupled at a common axle.

For simplicity, the drive cables 408a-d, the electrical conductor 422, the first and second ends 420a,b of the jaw cable 418 (FIGS. 4 and 5), and the drive rod 430 are each depicted in FIGS. 6A-6B as dashed lines. The drive cables 408a-d pass through portions (e.g., apertures 412) of the wrist 206 and terminate at the distal linkage 402a. The proximal linkage 402c may provide or otherwise define longitudinal grooves 604 that accommodate each drive cable 408a-d, and each groove 604 may receive a corresponding one of the drive cables 408a-d. The grooves 604 may be aligned with the corresponding apertures 412 defined by the proximal linkage 402c.

The wrist 206 provides or defines a central channel 606 that extends between the distal and proximal ends 602a,b. In embodiments where the wrist 206 includes the distal, intermediate, and proximal linkages 402a-c, corresponding portions of the central channel 606 may be cooperatively and successively defined by each linkage 402a-c. However, in embodiments where the wrist 206 includes only the distal and proximal linkages 402a,c, the central channel 606 may be defined cooperatively and successively by only the distal and proximal linkages 402a,c. The portions of the central channel 606 defined by each linkage 402a-c may coaxially align when the wrist 206 is non-articulated, but move out of axial alignment when the wrist 206 is moved in articulation.

The wrist 206 may further include a flexible member 608 positionable within the central channel 606 and extending at least partially between the first and second ends 602a-b of the wrist 206. As best seen in FIG. 6B, the flexible member 608 may provide or otherwise define one or more conduits 610 (four shown) that extend through the entire length of the flexible member 608. Consequently, the flexible member 608 may be referred to as a "multilumen" or a "multilumen element." The conduits 610 may be configured to receive the electrical conductor 422, the first and second ends 420a,b of the jaw cable 418 (FIGS. 4 and 5), and the drive rod 430, collectively referred to herein as "central actuation members." Accordingly, the central actuation members may penetrate the wrist 206 by extending through the conduits 610 of the flexible member 608.

In some embodiments, as illustrated, the conduits 610 may exhibit a circular cross-sectional shape, but could alternatively exhibit other cross-sectional shapes, such as polygonal, oval, or ovoid, without departing from the scope of the disclosure. Moreover, one or more of the conduits 610 may be lined with a material that helps mitigate abrasion and friction, such as nylon, silicone, nitinol, etc. Furthermore, the size (diameter) of the conduits 610 may vary, depending on the application. Those skilled in the art will readily appreciate that the shape, material, and size of the conduits 610 may be altered or otherwise customized consistent with known industry practices, without departing from the scope of the disclosure.

The flexible member 608 may be operatively coupled to the distal linkage 402a at its distal end, but may be free to move axially relative to the proximal linkage 402c at its proximal end. In some embodiments, for example, the wrist 206 may include a distal adapter 612 (FIG. 6A) and a proximal adapter 614 (FIG. 6B). The distal adapter 612 may operatively couple the flexible member 608 to the distal linkage 402a, and the proximal adapter 612 may be configured to support the flexible member 608 in sliding axial engagement with the proximal linkage 402c. In at least one embodiment, however, the proximal adapter 612 may be omitted and the flexible member 608 may directly contact the proximal linkage 402c in sliding engagement.

Figure 7A:
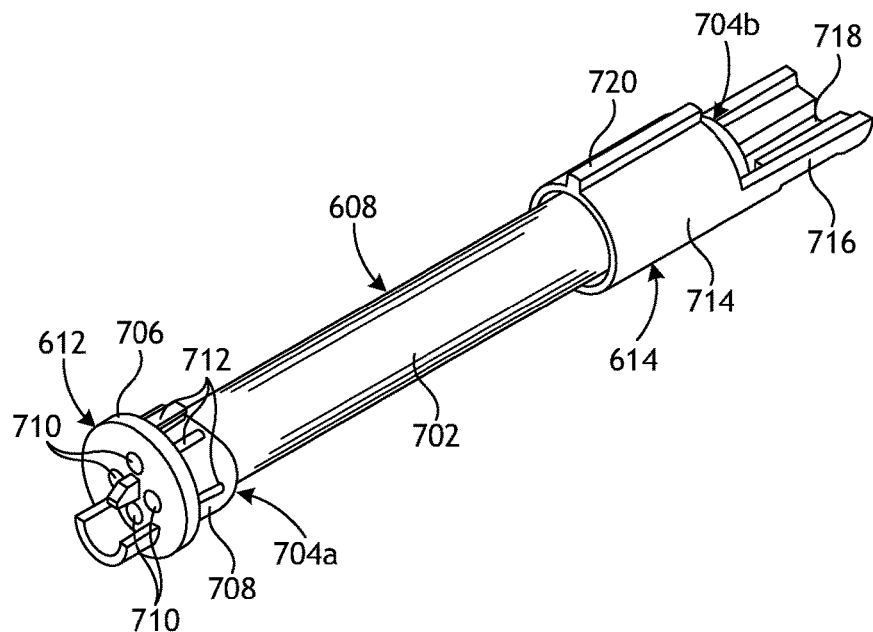
FIGS. 7A and 7B are isometric and exploded views, respectively, of the flexible member and the distal and proximal adapters of FIGS. 6A-6B, according to one or more embodiments.
Figure 7B:
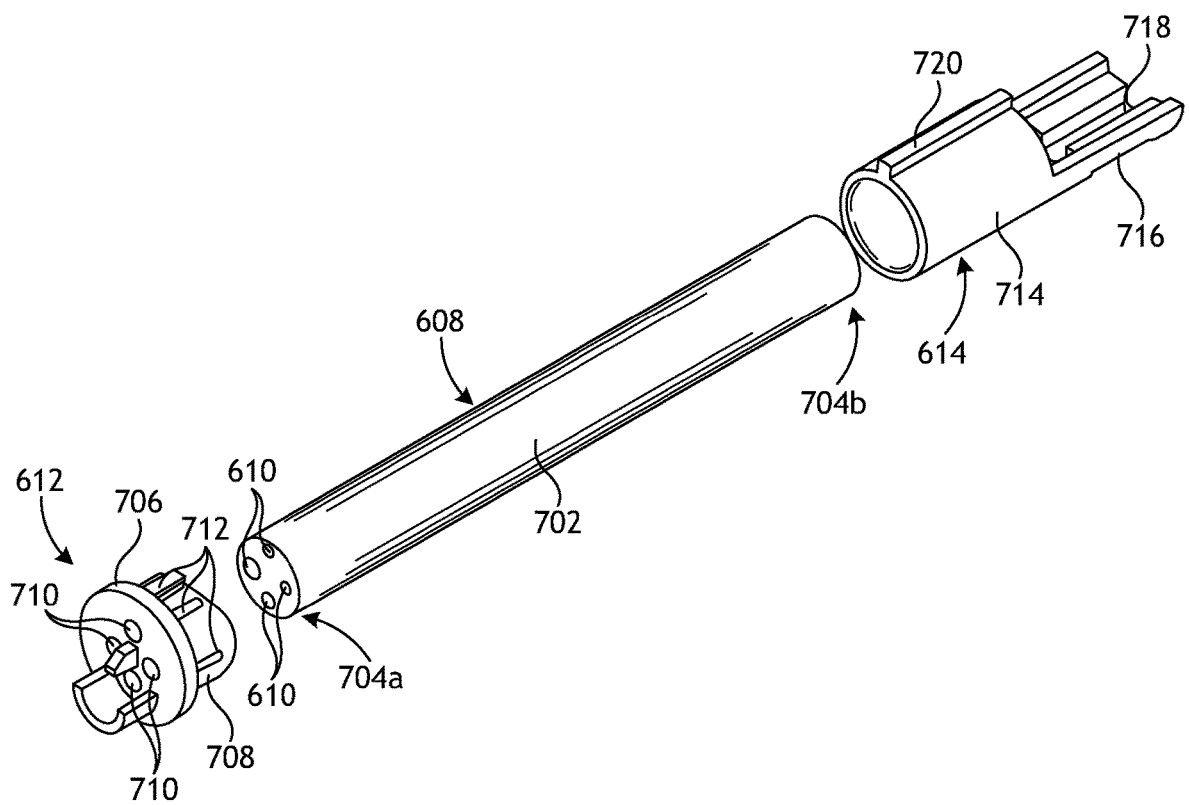

FIGS. 7A and 7B are isometric and exploded views, respectively, of the flexible member 608 and the distal and proximal adapters 612, 614, according to one or more embodiments. As illustrated, the flexible member 608 may comprise a generally cylindrical body 702 having a first or "distal" end 704a and a second or "proximal" end 704b opposite the distal end 704a. In some embodiments, as illustrated, the body 702 may exhibit a substantially circular cross-section, but may alternatively exhibit other cross-sectional shapes, such as polygonal (e.g., triangular, rectangular, etc.), polygonal with rounded corners, oval, ovoid, or any combination thereof, without departing from the scope of the disclosure.

The flexible member 608 may be made of any flexible or semi-flexible material that allows the flexible member 608 to flex or bend when the wrist 206 (FIGS. 6A-6B) articulates. Suitable materials for the flexible member 608 include, but are not limited to, polytetrafluoroethylene (PTFE or TEFLON®), silicone, nylon, a thermoplastic polyurethane (TPU, e.g., CARBOTHANE™, PELLETHANE®, TECOBAX™), a thermoplastic elastomer (TPE, e.g., PEBAX®), or any combination thereof. In some embodiments, the flexible member 608 can be manufactured from a plastic resin blended with a lubricant, such as PTFE solid particles blended with PROPEL® as a liquid lubricating additive.

The material for the flexible member 608 may also exhibit low friction characteristics or may otherwise be lubricious, which may prove advantageous in minimizing friction caused by the central actuation members (e.g., the electrical conductor 422, the first and second ends 420a,b of the jaw cable 418, and the drive rod 430 of FIGS. 6A-6B) extending through the conduits 610. Alternatively, the outside diameter of one or more of the central actuation members, such as the first and second ends 420a,b of the jaw cable 418, or the inside diameter of the conduits 610 may be coated with medical grade grease (e.g., KRYTOX™) to reduce contact friction. Furthermore, the material for the flexible member 608 may also exhibit good wear characteristics so the central actuation members do not inadvertently cut through the corresponding conduits 610 following repeated use. The diameter or size of each conduit 610 may be large enough to enable the central actuation members to move therein without substantive obstruction (friction), but small enough to support the central actuation members for longitudinal movement.

The distal adapter 612 may be made of a rigid or semi-rigid material including, but not limited to, a plastic, a metal, a composite material, and any combination thereof. Example materials for the distal adapter 612 include, but are not limited to, polyetherimide, polycarbonate, polystyrene, and nylon. In some embodiments, as illustrated, the distal adapter 612 may provide or otherwise define a radial shoulder 706 and a flange 708 that extends from the radial shoulder 706. The flange 708 may be sized to receive the distal end 704a of the flexible member 608. In other embodiments, however, the flange 708 may be omitted and the distal adapter 612 may nonetheless be coupled to the flexible member 608.

The distal adapter 612 may be coupled (fixed) to the distal end 704a of the flexible member 608 via a variety of attachment means. Suitable attachment means include, but are not limited to, bonding (e.g., an adhesive), welding (e.g., sonic or ultrasonic welding), overmolding the distal adapter 612 onto the distal end 704a, an interference or shrink fit, or any combination thereof.

The distal adapter 612 may define one or more or apertures 710 (four shown) configured to co-axially align with the conduits 610 of the flexible member 608. Accordingly, the central actuation members extending through the flexible member 608 (e.g., the electrical conductor 422, the first and second ends 420a,b of the jaw cable 418, and the drive rod 430 of FIGS. 6A-6B) may each exit the flexible member 608 and extend through the distal adapter 612 at the apertures 710.

In some embodiments, the distal adapter 612 may provide one or more features 712 configured to mate with one or more corresponding features of the distal linkage 402a (FIGS. 6A-6B). In the illustrated embodiment, the features 712 are defined on the flange 708, but could alternatively be defined on any other portion of the distal adapter 612, without departing from the scope of the disclosure. Mating the features 712 of the distal adapter 612 with the corresponding features of the distal linkage 402a may help rotationally fix the distal end 704a of the flexible member 608 at the distal end 602a (FIGS. 6A-6B) of the wrist 206 (FIGS. 6A-6B).

The proximal adapter 614 may be made of a rigid or semi-rigid material including, but not limited to, a plastic, a metal, a composite material, or any combination thereof. Example materials for the proximal adapter 614 include, but are not limited to, polyetherimide, polycarbonate, polystyrene, and nylon. The proximal adapter 614 may provide a generally annular body 714 sized to receive the proximal end 704b of the flexible member 608. In some embodiments, the proximal end 704b may extend entirely through the annular body 714, but may alternatively extend only partially therethrough.

The proximal adapter 614 may be coupled (fixed) to the proximal end 704b of the flexible member 608 via a variety of attachment means. Suitable attachment means include, but are not limited to, bonding (e.g., an adhesive), welding (e.g., sonic or ultrasonic welding), overmolding the proximal adapter 614 onto the proximal end 704b, an interference or shrink fit, or any combination thereof.

In some embodiments, a flange 716 may extend proximally from the body 714 of the proximal adapter 614 and may provide or define a groove 718 co-axially alignable with one of the conduits 610. The groove 718 may be sized to receive one of the central actuation members, such as the drive rod 430 (FIGS. 5 and 6A-6B), which may prove advantageous in helping to prevent buckling of the drive rod 430 during operation.

The proximal adapter 614 may provide one or more features 720 matable with one or more corresponding features provided by the proximal linkage 402c (FIGS. 6A-6B). As discussed in more detail below, the feature 720 may comprise a longitudinal rib that may be configured to mate with a longitudinal channel of the proximal linkage 402c.

Referring again to FIGS. 6A-6B, in some embodiments, the distal adapter 612 may be partially received within the central channel 606 defined in the distal linkage 402a. More specifically, the flange 708 (see FIG. 6B) of the distal adapter 612 may extend into the central channel 606 until the radial shoulder 706 (see FIG. 6A) of the distal adapter 612 engages the distal end 602a of the wrist 206 and, more particularly, the distal linkage 402a. In some embodiments, one or more features (not shown) may be defined on the inner radial surface of the central channel 606 at the distal linkage 402a and configured to mate with the features 712 (FIGS. 7A-7B) of the distal adapter 612. Mating these features may help rotationally fix the distal adapter 612 relative to the distal end 602a (FIGS. 6A-6B) of the wrist 206 (FIGS. 6A-6B).

The distal adapter 612 may be arranged to interpose the lower jaw 212 (FIG. 4) and the distal linkage 402a within the assembly of the end effector 204 (FIGS. 4-5), thus restraining (trapping) the distal adapter 612 between the lower jaw 212 and the distal linkage 402a. Since the distal adapter 612 may be fixed to the distal end 704a (FIGS. 7A-7B) of the flexible member 608, restraining (trapping) the distal adapter 612 between the lower jaw 212 and the distal linkage 402a may correspondingly fix the flexible member 608 in place at the distal end 602a of the wrist 206.

Referring specifically to FIG. 6B, the proximal linkage 402c may provide or define a feature 618 sized and otherwise configured to receive (mate with) the feature 720 provided by the proximal adapter 614. In the illustrated embodiment, the feature 618 comprises a longitudinal channel, and the feature 720 comprises a longitudinal rib matable with the longitudinal channel. Mating the features 618, 720 may help rotationally fix the flexible member 608 to the proximal linkage 402c, but also allows the flexible member 608 to move longitudinally relative to the proximal linkage 402c. For example, as the wrist 206 articulates, the feature 720 of the proximal adapter 614 may slide relative to the feature 618 of the proximal linkage 402c. In some embodiments, however, the proximal adapter 614 may be omitted and the feature 720 may alternatively be provided by the flexible member 608, without departing from the scope of the disclosure. In other embodiments, the flexible member 608 may be molded or otherwise formed in a shape that lends itself to be rotationally fixed to the proximal linkage 402c, such as a square or "D" shape.

In example operation of the wrist 206, the drive cables 408a-d are selectively actuated to articulate the wrist 206. As the wrist 206 articulates, the flexible member 608 correspondingly bends or flexes, and the central actuation members (e.g., the electrical conductor 422, the first and second ends 420a,b of the jaw cable 418, and the drive rod 430) will correspondingly move in the direction of articulation and thereby lengthen or shorten, depending on the bend direction. Extending the central actuation members through the conduits 610 of the flexible member 608 creates a defined and predictable pathway for each central actuation member.

Undesirable movement at the tip of the end effector 204 (FIG. 2) can occur when a high closure force is applied to the closure cable (e.g., the first end 420a of the jaw cable 418) to clamp the jaws 210, 212 onto tissue. This jaw tip motion is generated by slight off-center positional offsets of the closure cable at one or both of the articulation joints (i.e., the first and second pivot axes $P_1$, $P_2$ of FIGS. 4-5) during movement. This creates an unbalancing moment that can cause the jaws 210, 212 to move abruptly or "dive" in the direction of the imbalance. This "tip dive" is unexpected and undesirable when clamping critical structures.

According to embodiments of the present disclosure, one or more sub-articulation pivot guides may be included (installed) in the wrist 206 at the articulation joints to help contain and support the outer diameter of the flexible member 608 and thereby limit its ability to flex beyond the pivot axes $P_1$, $P_2$. As a result, the closure cable (or any of the central actuation members) will also be prevented from deviating below the pivot axes $P_1$, $P_2$ during actuation and tip dive will be mitigated. Similarly, the open cable may extend through a conduit 610 angularly offset 90° from the closure cable. The open cable interfaces with the sub-articulation pivot guide at the second articulation joint (i.e., the yaw axis) in the same manner as the closure cable. As the jaws 210, 212 are opened against resisting tissue, the tension in the open cable increases, and the potential for tip dive in the yaw axis increases. The sub-articulation pivot guide arranged at the second articulation joint will resist the offset moment and any resulting motion of the flexible member 608 in this direction.

Sub-Articulation Ring Optimized Bend Radius

FIG. 8A is an isometric side view of an example embodiment of a portion of the wrist 206 that may incorporate one or more principles of the present disclosure. In the illustrated view, the intermediate linkage 402b is shown in phantom to enable viewing of the inner component parts of the wrist 206. The distal and proximal linkages 402a,c (FIGS. 4-5), the drive cables 408a-d (FIGS. 4-5), the electrical conductor 422 (FIGS. 4-5), the first and second ends 420a,b of the jaw cable 418 (FIGS. 4-5), and the drive rod 430 (FIGS. 4-5) are each omitted for simplicity, but would otherwise be included in a full assembly of the wrist 206.

As illustrated, the flexible member 608 extends through the central channel 606 partially defined by the intermediate linkage 402b. The first pivot axis $P_1$ extends through a first articulation joint 802a and facilitates "yaw" movement (articulation) of the end effector 204 (FIG. 2), and the second pivot axis $P_2$ extends through a second articulation joint 802b and facilitates "pitch" movement (articulation) of the end effector 204.

The wrist 206 further includes a first pivot guide 804a arranged at the first articulation joint 802a and a second pivot guide 804b arranged at the second articulation joint 802b. Each pivot guide 804a,b is rotatably mounted to the intermediate linkage 402b at the corresponding articulation joints 802a,b and is rotatable about the first and second pivot axes $P_1$, $P_2$, respectively. The pivot guides 804a,b may be made of any semi-rigid or flexible material including, but not limited to, a plastic, a metal, a composite material, an elastomer, or any combination thereof. Example non-metal materials include, but are not limited to, polyetherimide, polycarbonate, polystyrene, carbon filled polyphalamide (PPA), and nylon.

FIG. 8B is an enlarged isometric view of the intermediate linkage 402b. In the illustrated embodiment, the intermediate linkage 402b includes a main body 806 that defines a portion of the central channel 606 configured to accommodate the flexible member 608 (FIG. 8A). A pair of distally extending lobes 808a and 808b extend from the body 806 and are laterally offset from each other, and a pair of proximally extending lobes 810a and 810b extend from the body 806 and are laterally offset from each other. The proximally extending lobes 810a,b are angularly offset from the distally extending lobes 808a,b by 90°, which allows the intermediate linkage 402b to facilitate both "yaw" and "pitch" articulation of the end effector 204 (FIG. 2). Each lobe 808a,b and 810a,b defines an aperture 812 sized to rotatably receive a portion of the corresponding pivot guide 804a,b. Moreover, in the illustrate embodiment, the lobes 808a,b and 810a,b provide portions of the first and second axles 404a,b, respectively, to enable rotatable coupling to the distal and proximal linkages 402a,c (FIGS. 4-5).

FIG. 8C is an enlarged isometric view of the second pivot guide 804b. Since the first and second pivot guides 804a,b are substantially similar in structure and operation, discussion of the second pivot guide 804b will equally apply to the first pivot guide 804a. As illustrated, the second pivot guide 804b includes a generally annular body 814 that defines a central aperture 816 alignable with the central channel 606 (FIGS. 8A-8B) of the wrist 206 (FIG. 8A) and sized or otherwise configured to accommodate the flexible member 608 (FIG. 8A) therethrough. Opposing pins 818 may extend radially outward from the annular body 814 at angularly opposite sides of the body 814. To secure the second pivot guide 804b to the intermediate linkage 402b, the pins 818 may be rotatably received into the apertures 812 defined on the proximally extending lobes 810a,b (FIG. 8B) of the intermediate linkage 402b (FIG. 8B).

Referring again to FIG. 8A, example operation of the wrist 206 will now be provided, according to one or more embodiments. As illustrated, the flexible member 608 is extended through the central channel 606 of the wrist 206 and also through the central aperture 816 of each pivot guide 804a,b. The first and second ends 420a,b of the jaw cable 418 are shown as dashed lines extending through corresponding conduits 610 defined through the flexible member 608. As depicted, the wrist 206 is being articulated in pitch motion at the second articulation joint 802b and otherwise moved about the second pivot axis $P_2$. Moving the second articulation joint 802b correspondingly causes the second pivot guide 804b to rotate about the second pivot axis $P_2$ to accommodate bending of the flexible member 608 from a straight position. As the angle at the second articulation joint 802b deviates from straight, the flexible member 608 and the closure cable (i.e., the first end 420a of the jaw cable 418) will tend to find the shortest path through the second articulation joint 802b, which can urge the flexible member 608 and the closure cable to dip below the second pivot axis $P_2$, which can cause tip dive if the closure cable is actuated.

The second pivot guide 804b, however, helps to contain and support the outer diameter of the flexible member 608 at the second articulation joint 802b and thereby prevents the flexible member 608 from flexing beyond the second pivot axis $P_2$. Consequently, the centerline of the closure cable (i.e., the first end 420a of the jaw cable 418) will also not be able to deviate below the second pivot axis $P_2$ during clamping, which will mitigate tip dive at the end effector 204 (FIG. 2).

Figure 9A:
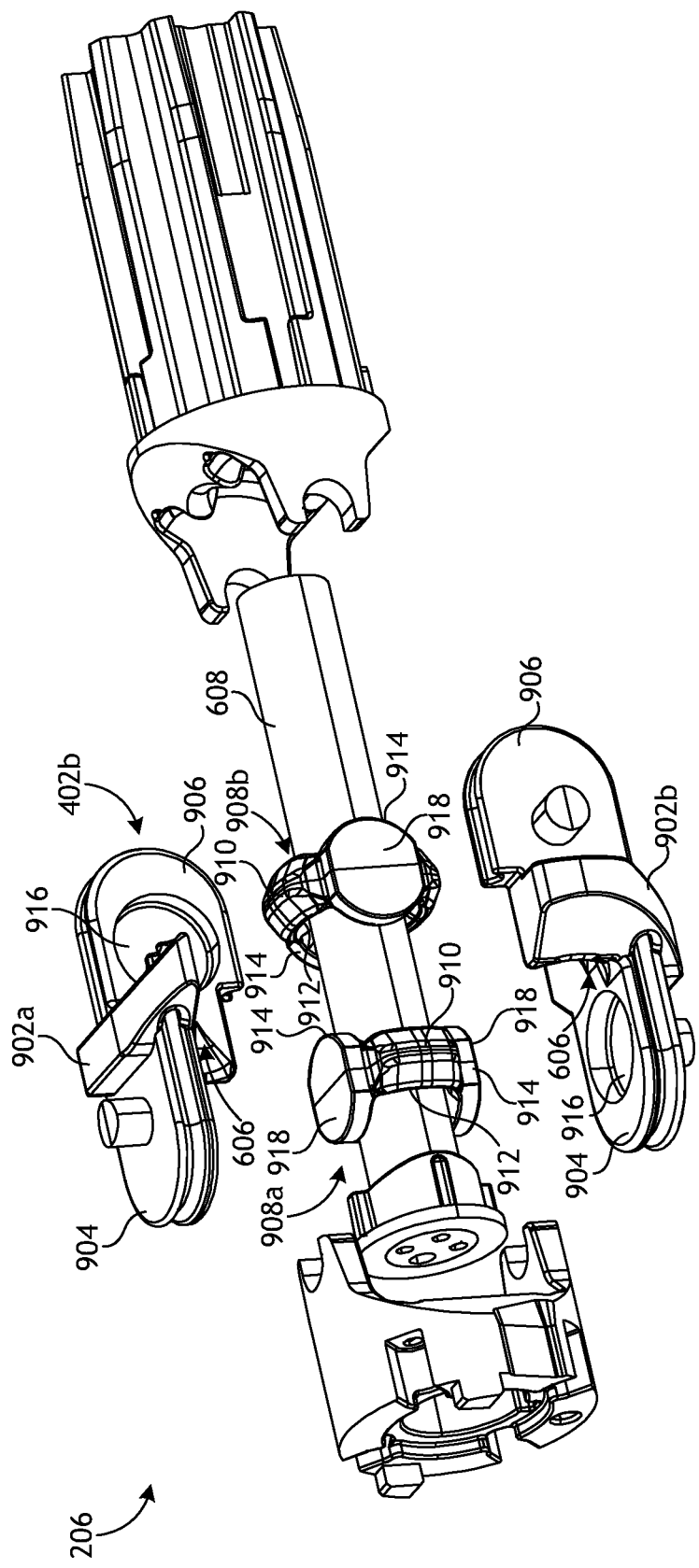
FIG. 9A is an isometric side view of another example embodiment of a portion of the wrist of FIGS. 4, 5, and 6A-6B that may incorporate one or more principles of the present disclosure.

FIG. 9A is an exploded view of another example embodiment of the wrist 206, according to one or more additional embodiments. For simplicity, the drive cables 408a-d (FIGS. 4-5), the electrical conductor 422 (FIGS. 4-5), the first and second ends 420a,b of the jaw cable 418 (FIGS. 4-5), and the drive rod 430 (FIGS. 4-5) are each omitted in FIG. 9A. In the present embodiment, the intermediate linkage 402b is made of two or more pieces or component parts, shown in the illustrated embodiment as a first intermediate part 902a and a second intermediate part 902b. The first and second intermediate parts 902a,b may comprise identical elements or mirror images of each other and are matable to form the intermediate linkage 402b and thereby help define a portion of the central channel 606 through which the flexible member 608 can extend. While only two intermediate parts 902a,b are depicted in FIG. 9A, the intermediate linkage 402*b* may alternatively comprise three or more intermediate parts, without departing from the scope of the disclosure.

Each intermediate part 902*a,b* may provide a distally extending lobe 904 and a proximally extending lobe 906 that extends orthogonal to the distally extending lobe 904. When the intermediate parts 902*a,b* are mated to form the intermediate linkage 402*b*, the distally extending lobes 904 will be laterally offset from each other and the proximally extending lobes 906 will be laterally offset from each other and angularly offset from the distally extending lobes 906 by 90°, which allows the intermediate linkage 402*b* to facilitate both "yaw" and "pitch" articulation of the end effector 204 (FIG. 2).

As illustrated, the wrist 206 may further include first and second pivot guides 908*a* and 908*b* that may be secured upon mating the first and second intermediate parts 902*a,b*. Each pivot guide 908*a,b* includes a generally annular body 910 that defines a central aperture 912 alignable with the central channel 606 of the wrist 206 and sized or otherwise configured to accommodate the flexible member 608. Internal surfaces of the central aperture 912 may be smoothed, curved, and/or employ a lubricant, which may help improve articulation joint friction and reduce galling in the surgical tool 200 (FIG. 2), thus increasing device mission life. Opposing heads 914 may be positioned at angularly opposite sides of the annular body 910 of each pivot guide 908*a,b*. Each head 914 may be generally disc-shaped and configured to be received within a corresponding bearing pocket 916 defined on an opposing lobe 904, 906 of the intermediate linkage 402*b*. The heads 914 may be configured to rotate within the bearing pockets 916 during operation as the flexible member 608 bends and flexes. Each head 914 may define or otherwise provide a bearing face 918 engageable with the bottom of the adjacent bearing pocket 916.

Figure 9B:
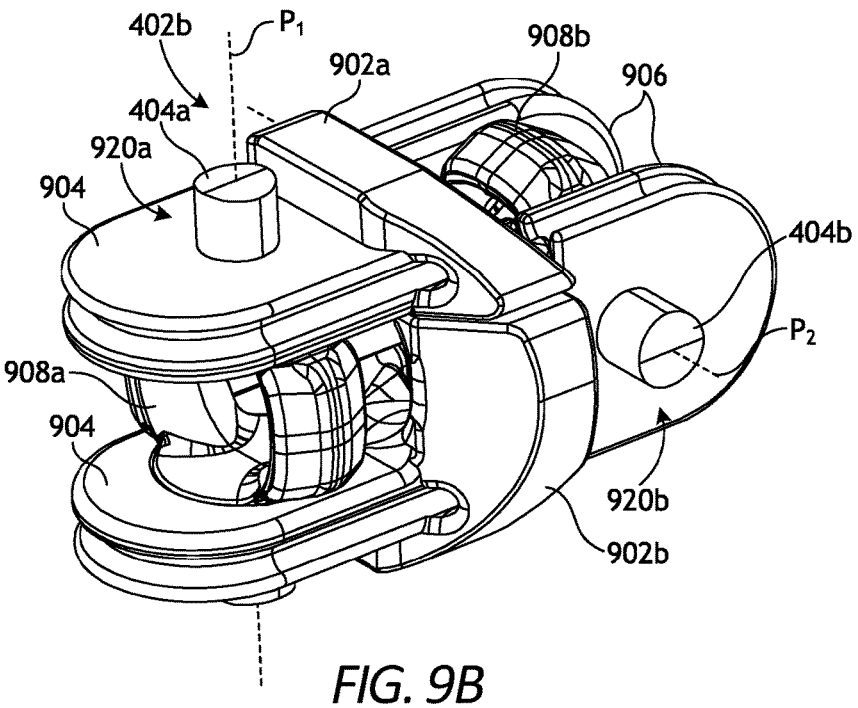
FIG. 9B is an enlarged isometric view of another embodiment of the intermediate linkage of FIG. 9A.

FIG. 9B is an assembled, isometric view of the intermediate linkage 402*b* of FIG. 9A. As illustrated, opposite portions of the first axle 404*a* may be defined on the distally extending lobes 904 and provide a first articulation joint 920*a*, and opposing portions of the second axle 404*b* may be defined on the proximally extending lobes 906 and provide a second articulation joint 920*b*. Moreover, the first pivot axis $P_1$ extends through the first articulation joint 920*a* and facilitates "yaw" movement (articulation) of the end effector 204 (FIG. 2), and the second pivot axis $P_2$ extends through the second articulation joint 920*b* and facilitates "pitch" movement (articulation) of the end effector 204.

The first and second intermediate parts 902*a,b* may be made of any rigid or semi-rigid material including, but not limited to, a plastic, a metal, a composite material, an elastomer, or any combination thereof. In at least one embodiment, the first and second intermediate parts 902*a,b* may be made of a metal and manufactured through metal injection molding with some post machining on critical surfaces and/or pivoting locations. The first and second intermediate parts 902*a,b* may be permanently or removably secured together to form the intermediate linkage 402*b*. Suitable securing methods include, but are not limited to, welding, an adhesive attachment, one or more mechanical fasteners, or any combination thereof. In other embodiments, securing the first and second intermediate parts 902*a,b* together may not be required since once the distal and proximal linkages 402*a,c* (FIG. 9A) are rotatably coupled to the intermediate linkage 402*b*, the first and second intermediate parts 902*a,b* will be trapped in place by the distal and proximal linkages 402*a,c*.

The first and second pivot guides 908*a,b* will be secured to the intermediate linkage 402*b* upon mating the first and second intermediate parts 902*a,b*. The first pivot guide 908*a* is rotatably secured at the first articulation joint 920*a*, and the second pivot guide 908*b* is rotatably secured at the second articulation joint 920*b*. Moreover, the pivot guides 908*a,b* are rotatable about the first and second pivot axes $P_1$, $P_2$. The pivot guides 908*a,b* may be made of any of the materials mentioned herein for the pivot guides 804*a,b* of FIG. 8A.

Figure 9C:
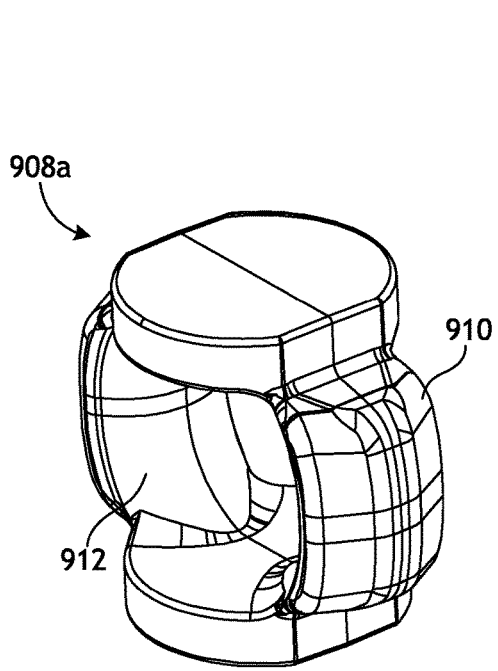
FIG. 9C is an isometric view of the first pivot guide of FIG. 9B
Figure 9D:
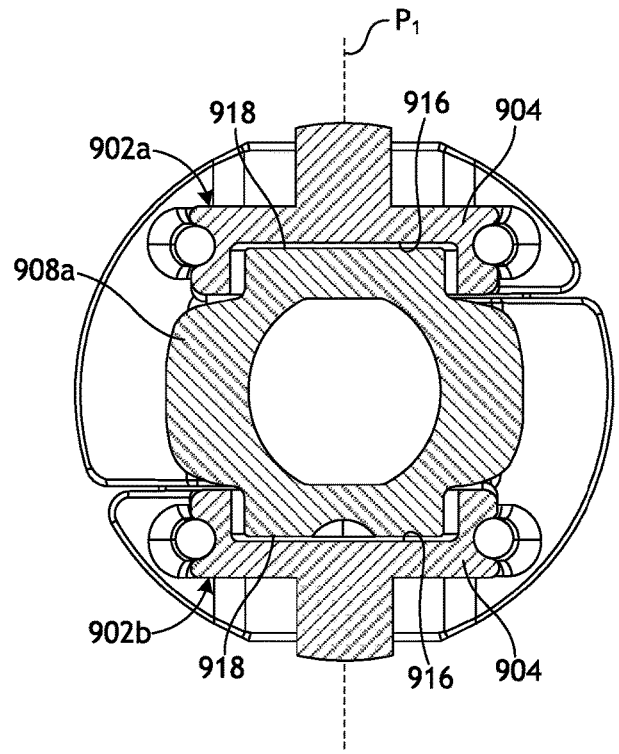
FIG. 9D is a cross-sectional end view of the first pivot guide of FIG. 9B.

FIG. 9C is an isometric view of the first pivot guide 908*a* and FIG. 9D is a cross-sectional end view of the first pivot guide 908*a* secured between the proximally extending lobes 904 of the first and second intermediate parts 902*a,b*. As illustrated in FIG. 9B, the bearing faces 918 are received within the corresponding bearing pockets 916 and help the first pivot guide 908*a* rotate about the first pivot axis $P_1$ as the flexible member 608 (FIG. 9A) bends and flexes during operation. In at least one embodiment, one or both of the bearing faces 918 or the bottom of the pockets 916 may be polished and/or employ a lubricant, which may help reduce friction and galling as the pivot guide 908*a* rotates during operation.

As best seen in FIG. 9C, the annular body 910 of the first pivot guide 908*a* is enlarged radially and is thicker as compared to the first and second pivot guides 804*a,b* of FIG. 8A. Because the first and second intermediate parts 902*a,b* comprise independent component parts that are matable to secure the first pivot guide 908*a*, wider and larger designs of the first pivot guide 908*a* can be accommodated and the first and second intermediate parts 902*a,b* will be mated about the larger designs. This may prove advantageous in providing additional strength to the system. Moreover, enlarging the size of the pivot guide 908*a* allows the contact radius of the central channel 912 to also be enlarged. This will increase the radius of the arcuate surface where the elongate member 608 (and the central actuation members) contacts and bends around during articulation. Consequently, this will reduce flexure fatigue loading on the elongate member 608 and extend service life.

Articulation Capstan Tension Retainment Using Ratchet Clutch Mechanism

Figure 10:
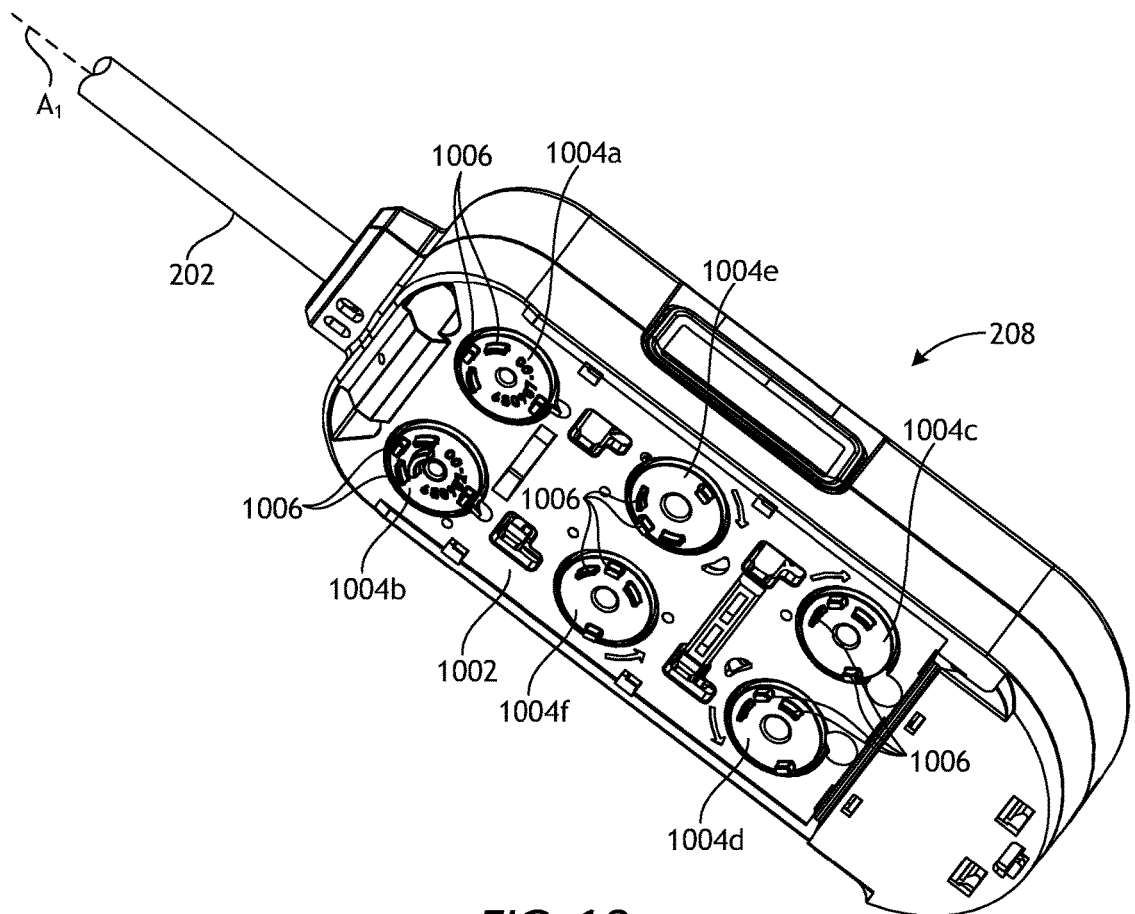
FIG. 10 is a bottom view of the drive housing of FIG. 2, according to one or more embodiments.

FIG. 10 is a bottom view of the drive housing 208, according to one or more embodiments. As illustrated, the drive housing 208 may include a tool mounting interface 1002 used to operatively couple the drive housing 208 to a tool driver of a robotic manipulator. The tool mounting interface 1002 may releasably couple the drive housing 208 to a tool driver in a variety of ways, such as by clamping thereto, clipping thereto, or slidably mating therewith. The tool mounting interface 1002 may include an array of electrical connecting pins, which may be coupled to an electrical connection on the mounting surface of the tool driver. Accordingly, the tool mounting interface 1002 may mechanically, magnetically, and/or electrically couple the drive housing 208 to the tool driver.

As illustrated, the interface 1002 includes and supports a plurality of inputs, shown as drive inputs 1004*a*, 1004*b*, 1004*c*, 1004*d*, 1004*e*, and 1004*f*. Each drive input 1004*a-f* may comprise a rotatable disc configured to align with and couple to a corresponding actuator of a given tool driver. Moreover, each drive input 1004*a-f* may provide or define one or more surface features 1006 configured to align and mate with corresponding features provided on the given actuator. The surface features 1006 can include, for example, various protrusions and/or indentations that facilitate a mating engagement. Each of the drive inputs 1004*a-f* may be actuated based on user inputs communicated to a tool driver coupled to the interface 1002, and the user inputs may be received via a computer system incorporated into the robotic surgical system.

In some embodiments, actuation of the first drive input 1004a may be configured to control rotation of the shaft 202 about the longitudinal axis $A_1$. The shaft 202 may be rotated clockwise or counter-clockwise depending on the rotational direction of the first drive input 1004a. In some embodiments, actuation of the second drive input 1004b may be configured to advance or retract the knife 426 (FIG. 4). In some embodiments, actuation of the third and fourth drive inputs 1004c,d may be configured to open and close the jaws 210, 212 (FIG. 4). More specifically, the first and second ends 420a,b (FIG. 4) of the jaw cable 418 (FIG. 4) may extend to and be operatively coupled to a corresponding one of the third and fourth drive inputs 1004c,d such that cooperative actuation of the third and fourth drive inputs 1004c,d causes the jaw cable 418 to open/close the jaws 210, 212.

In some embodiments, actuation of the fifth and sixth drive inputs 1004e,f may be configured to axially translate the drive cables 408a-d (FIG. 4), and thereby articulate the end effector 204 (FIG. 4). More specifically, two drive cables 408a-d may be operatively coupled to each drive input 1004e,f such that actuation of the fifth drive input 1004e causes two of the drive cables 408a-d to axially translate, and actuation of the sixth drive input 1004f causes the other two drive cables 408a-d to axially translate. In one embodiment, for example, the second and third drive cables 408b,c may be driven by actuation of the fifth drive input 1004e, and the first and fourth drive cables 408a,d may be driven by actuation of the sixth drive input 1004f.

Figure 11:
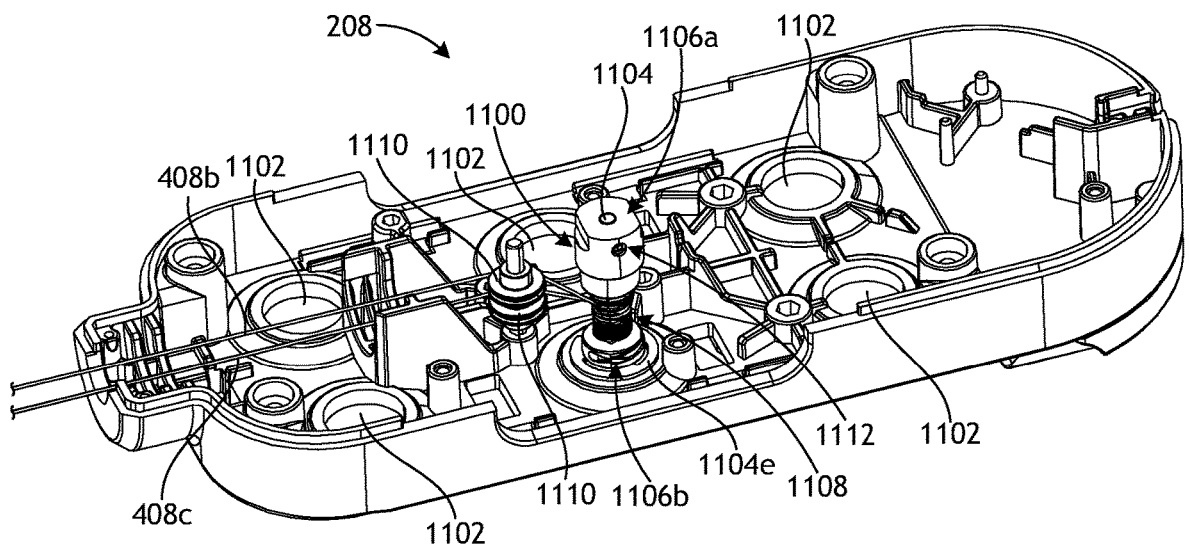
FIG. 11 is an isometric exposed view of the interior of the drive housing of the surgical tool of FIG. 10.

FIG. 11 is an isometric exposed view of the interior of the drive housing 208, according to one or more embodiments. Several component parts that would otherwise be contained within the drive housing 208 are not depicted in FIG. 11 for simplicity and to enable discussion of the remaining depicted component parts. More particularly, FIG. 11 depicts a drive assembly 1100 associated with the fifth drive input 1004e, and several holes 1102 are defined in the drive housing 208 where additional drive assemblies (not shown) would otherwise be mounted to the drive housing 208 and associated with the first, second, third, fourth, and sixth drive inputs 1004a-d and f, respectively.

The drive assembly 1100 may include or otherwise be mounted to an input shaft 1104. The input shaft 1104 is operatively coupled to or extends from the fifth drive input 1004e such that actuation of the fifth drive input 1004e correspondingly rotates the input shaft 1104 and operates the drive assembly 1100.

The drive assembly 1100 also includes a first or "upper" capstan 1106a and a second or "lower" capstan 1106b. In at least one embodiment, the input shaft 1104 may form an integral part or extension of the lower capstan 1106b, but the lower capstan 1106b may alternatively be mounted to the input shaft 1104. The upper capstan 1106a may be matable with the lower capstan 1106b at a clutch feature 1108 movable between a first or "engaged" position and a second or "disengaged" position. As described in more detail below, when the clutch feature 1108 is in the engaged position, rotation of the input shaft (via actuation of the fifth drive input 1004e) correspondingly rotates the capstans 1106a,b in unison in the same angular direction. In contrast, when the clutch feature 1108 is in the disengaged position, the upper and lower capstans 1106a,b may be able to rotate independent of the other in at least one angular direction.

Each of the capstans 1106a,b may have a drive cable coupled thereto (i.e., wrapped thereabout) and extending therefrom. In the illustrated embodiment, the second drive cable 408b is coupled to the upper capstan 1106a and the third drive cable 408c is coupled to the lower capstan 1106a. Each drive cable 408b,c extends from the corresponding capstan 1106a,b, out of the drive housing 208, and to the end effector 204 (FIG. 2). In some embodiments, as illustrated, each drive cable 408b,c may be routed around an idler pulley 1110 that redirects the corresponding drive cable 408b,c between the shaft 202 (FIG. 10) and the respective capstan 1106a,b. As will be appreciated, the second and third drive cables 408b,c may alternatively be coupled to the opposite capstan 1106a,b, without departing from the scope of the disclosure. Moreover, any combination of two of the drive cables 408a-d of FIG. 4 may be coupled to the capstans 1106a,b, in accordance with this disclosure.

In example operation, with the clutch feature 1108 in the engaged position, the fifth drive input 1004e is actuated to rotate the input shaft 1104, which correspondingly rotates the capstans 1106a,b in unison in the same angular direction. As the capstans 1106a,b rotate, the drive cables 408a,b operate in an antagonistic, closed-loop system that causes the end effector 204 (FIG. 2) to articulate at the wrist 206 (FIG. 2) in at least one degree of motion. Prior to operation, however, the drive cables 408b,c need to be pre-tensioned to ensure proper articulation operation. According to embodiments described herein, this may be accomplished by moving (transitioning) the clutch feature 1108 to the disengaged position and rotating the capstans 1106a,b in opposite angular directions until a predetermined amount of tension is achieved in the drive cables 408b,c. When the desired tension (torque) has been reached, the clutch feature 1108 may then be moved (transitioned) to the engaged position, which operatively couples the upper and lower capstans 1106a,b for simultaneous rotation and operation.

In at least one embodiment, a setting feature 1112 may be used to lock the clutch feature 1108 in the engaged position and otherwise prevent axial separation or movement of the capstans 1106a,b, which would disengage the clutch feature 1108. In the illustrated embodiment, the setting feature 1112 comprises a pin, set screw, or the like received within the upper capstan 1106a and configured to interface with a recess (not shown), such as a molded opening, defined in the lower capstan 1106b or the input shaft 1104. In other embodiments, however, the setting feature 1112 may comprise a portion or feature (e.g., a boss, a receptacle, etc.) of the drive housing 208. In such embodiments, the drive housing 208 may be assembled such that the top portion of the drive housing 208 may engage the upper capstan 1106a and thereby prevent axial separation or movement of the upper capstan 1106a away from the lower capstan 1106b, thus preventing disengagement of the clutch feature 1108. With the setting feature 1112 engaged, axial separation of the capstans 1106a,b is inhibited, which helps retain the articulation cable pre-tension.

FIGS. 12A and 12B are isometric assembled and exploded views of one example of the drive assembly 1100, according to one or more embodiments. In the illustrated embodiment, the drive cables 408b,c (FIG. 11) are omitted for simplicity, but would otherwise be wrapped around and coupled to the respective capstans 1106a,b at corresponding crimp pockets 1202 (one shown) provided on each capstan 1106a,b. The input shaft 1104 (FIG. 12B) extends from the fifth drive input 1004e and may form an integral part or extension of the lower capstan 1106b.

In the illustrated embodiment, the clutch feature 1108 comprises a plurality of angled, interlocking ratchet teeth 1204 defined on both capstans 1106a,b. When the clutch feature 1108 is in the disengaged position, the ratchet teeth 1204 allow the capstans 1106a,b to rotate (ratchet) relative to the other in opposite angular directions until a predetermined amount of tension is achieved in the drive cables 408b,c (FIG. 11) for operation. In some embodiments, the upper capstan 1106a may be rotated relative to the lower capstan 1106b to apply tension to the drive cables 408b,c. This may be accomplished by rotating the upper capstan 1106a at a head 1206, which in the illustrated embodiment comprises a hexagonal feature. In other embodiments, however, the lower capstan 1106b may be rotated relative to the upper capstan 1106a to apply tension to the drive cables 408b,c. This may be accomplished by rotating the fifth drive input 1004e, which rotates the lower capstan 1106b relative to the upper capstan 1106a. In yet other embodiments, the capstans 1106a,b may be rotated in opposite directions simultaneously to apply tension to the drive cables 408b,c, without departing from the scope of the disclosure.

The large number of ratchet teeth 1204 about the circumference of each capstan 1006a,b provides sufficient strength to endure loading conditions imparted by the tension in the cables 408b,c. Moreover, the large number of ratchet teeth 1204 provide sufficient strength that allows the capstans 1006a,b to be made of less expensive materials, such as plastics and composites. The large number of ratchet teeth 1204 may also allow for fine tuning or resolution of the tension in the drive cables 408a,b. For example, a clutch feature 1108 having thirty or more ratchet teeth 1204 may enable a drive cable pre-tension resolution of 4 N or less.

Upon moving the clutch feature 1108 to the engaged position, the ratchet teeth 1204 will be locked and thereby couple the upper and lower capstans 1106a,b for simultaneous rotation in the same angular direction, as dictated by rotation of the input shaft 1104. Accordingly, locking the ratchet teeth 1204 together with the clutch feature 1108 in the engaged position helps to retain tension in the cables 408b,c.

Once the specification for tension in the drive cables 408b,c (FIG. 11) has been met, the clutch feature 1108 may be transitioned (moved) to the engaged position and the setting feature 1112 may then be employed to prevent axial motion of either of the capstans 1106a,b to maintain tooth engagement. As described above, the setting feature 1112 may comprise a set screw or pin 1208 received within the upper capstan 1106a and configured to interface with a recess 1210 (FIG. 12B) defined in the lower capstan 1106b or the input shaft 1104. In the illustrated embodiment, the pin 1208 may be received within an aperture 1214 defined in the upper capstan 1106a and extending to the recess 1208 when the upper capstan 1106a is mounted to the input shaft 1104. With the setting feature 1112 engaged, axial separation of the capstans 1106a,b is inhibited, which helps retain articulation cable pre-tension.

In other embodiments, as mentioned above, the setting feature 1112 may alternatively comprise a portion or feature (e.g., a boss, a receptacle, etc.) of the drive housing 208 (FIGS. 10 and 11) that receives the head 1206 of the upper capstan 1106a when the drive housing 208 is assembled. Receiving the head 1206 into the portion or feature of the drive housing 208 may remove any clearance for axial motion between the upper capstan 1106a and the housing 208, which helps prevent axial separation of the upper capstan 1106a away from the lower capstan 1106b and thereby prevents disengagement of the clutch feature 1108.

FIGS. 13A and 13B are isometric assembled and exploded views of another example of the drive assembly 1100, according to one or more embodiments. In the illustrated embodiment, the drive cables 408b,c (FIG. 11) are again omitted for simplicity, but would otherwise be wrapped around and coupled to the respective capstans 1106a,b. As illustrated, the input shaft 1104 extends from the fifth drive input 1004e and may form an integral part or extension of the lower capstan 1106b. Moreover, the upper capstan 1106a may be mounted to the input shaft 1104.

In the illustrated embodiment, the clutch feature 1108 comprises matable geometric features defined on both capstans 1106a,b. More specifically, the upper capstan 1006a may provide or otherwise define a drive protrusion 1302 matable with a corresponding drive recess or pocket 1304 defined on the lower capstan 1006b, the drive protrusion and pocket 1302, 1304 each being arranged in a radial pattern and configured for carrying or transferring torsional load. In other embodiments, the drive protrusion 1302 may be defined on the lower capstan 1006b and the drive pocket 1304 may be defined on the upper capstan 1006a, without departing from the scope of the disclosure. In some embodiments, as illustrated, the drive protrusion 1302 may be in the form of gear teeth, castellations, flower petals, or any other geometric protruding design, and the drive pocket 1304 may be sized and otherwise formed to receive the drive protrusion 1302.

The clutch feature 1108 shown in FIGS. 13A-13B may operate similar to the clutch feature 1108 shown in FIGS. 12A-12B and, therefore, will not be described again in detail. Moreover, achieving a predetermined tension in the drive cables 408b,c (FIG. 11) using the drive assembly 1100 of FIGS. 13A-13B may be similar to achieving a predetermined tension in the drive cables 408b,c using the drive assembly 1100 of FIGS. 12A-12B and, therefore, will not be described again in detail.

In some embodiments, the setting feature 1112 (FIGS. 11 and 12A-12B) may be included in the drive assembly 1100 of FIGS. 13A-13B to help prevent axial separation or movement of either of the capstans 1106a,b and thereby maintain engagement between the drive protrusion and pocket 1302, 1304. In other embodiments, however, the setting feature 1112 may be omitted and the depth of the drive protrusion and pocket 1302, 1304 and related frictional engagement between the two features may be sufficient to prevent axial (vertical) motion between the capstans 1106a, b. In yet other embodiments, the setting feature 1112 may alternatively comprise a portion or feature (e.g., a boss, a receptacle, etc.) of the drive housing 208 (FIGS. 10 and 11) that receives the head 1206 of the upper capstan 1106a when the drive housing 208 is assembled. Receiving the head 1206 into the portion or feature of the drive housing 208 may remove any clearance for axial motion between the upper capstan 1106a and the housing 208, which helps prevents axial separation of the upper and lower capstans 1106a,b and thereby prevents disengagement of the clutch feature 1108.

Shaft Gear Castellation

Figure 14:
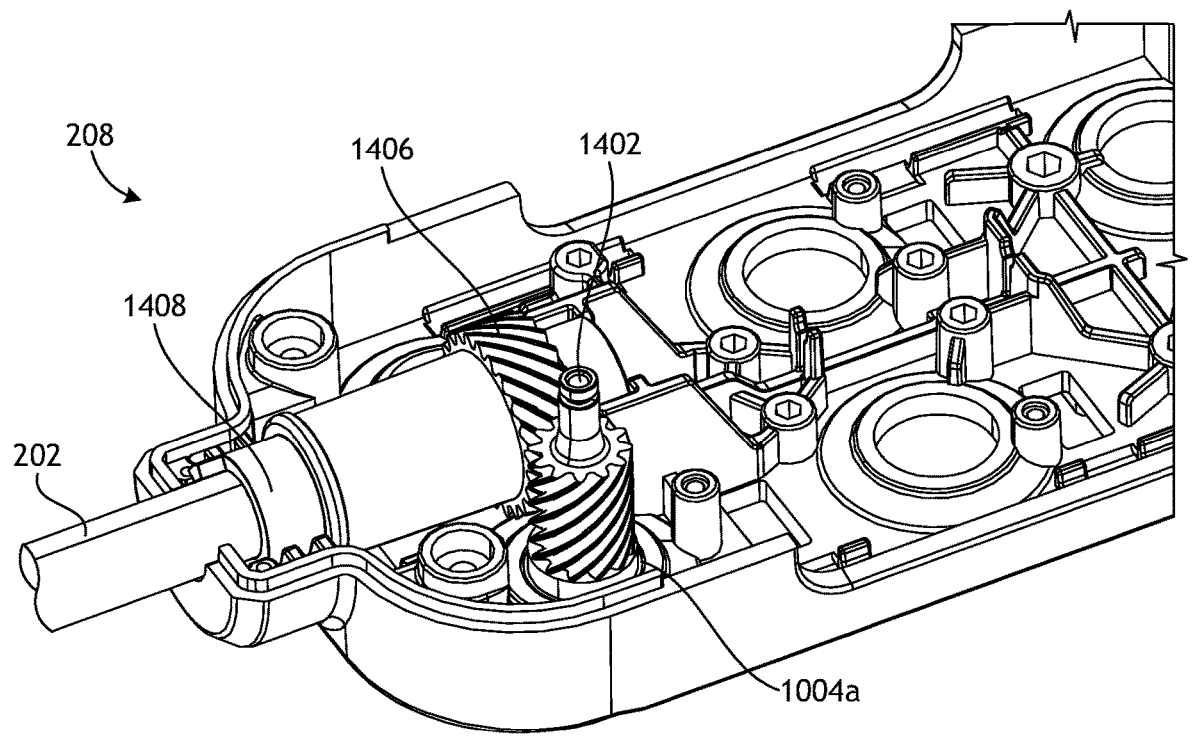
FIG. 14 is another isometric exposed view of the interior of the drive housing of FIG. 2, according to one or more additional embodiments.

FIG. 14 is another isometric exposed view of the interior of the drive housing 208, according to one or more additional embodiments. For simplicity and to enable discussion, several component parts that would otherwise be contained within the drive housing 208 are not depicted in FIG. 14. More particularly, FIG. 14 depicts a drive shaft 1402 extending from the first drive input 1004a. A helical drive gear 1404 is coupled to or forms part of the drive shaft 1402 such that rotation of the drive shaft 1402 correspondingly rotates the helical drive gear 1404 in the same direction. The helical drive gear 1406 may be arranged to intermesh with a driven roll gear 1406 mounted to the shaft 202. In operation, actuation of the first drive input 1004a rotates the helical drive gear 1404, which drives the roll gear 1406 and thereby causes the shaft 202 to be rotated (rolled) clockwise or counter-clockwise in positive or negative rotation, depending on the rotational direction of the first drive input 1004a.

The roll gear 1406 is rotationally coupled to the shaft 202 to enable transmission of torque from the roll gear 1406 to the shaft 202. In some applications, the roll gear 1406 is rotationally coupled to the shaft 202 via a castellated mating engagement. Current castellated coupling systems between the roll gear 1406 and the shaft 202, however, can often be assembled in an incorrect orientation. Moreover, because of the changes in direction and need for inherent ease of assembly of the roll gear 1406 to the shaft 202, there can be inherent backlash (e.g., dead motion) that occurs between the transmission from the roll gear 1406 to the shaft 202.

According to embodiments of the present disclosure, the roll gear 1406 may be rotationally coupled to the shaft 202 via a castellated interface that eliminates backlash within the device roll system, especially when changing roll directions. Moreover, the presently disclosed castellated interface includes self-locating features for roll system torque transmission, which can be advantageous in preventing incorrect assembly that would otherwise lead to device scrapping or a need to re-work the system.

Figure 15:
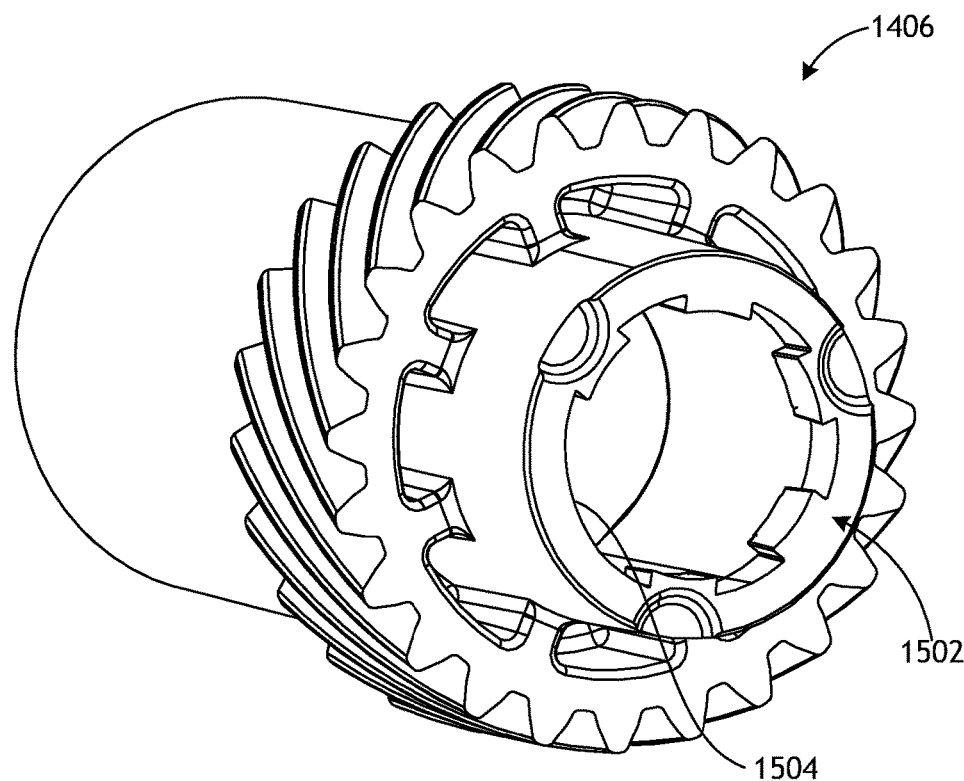
FIG. 15 is an isometric end view of one example of the roll gear of FIG. 14, according to one or more embodiments.

FIG. 15 is an isometric end view of one example of the roll gear 1406, according to one or more embodiments. In the illustrated embodiment, a castellated interface 1502 is defined on an inner surface of the roll gear 1406 and designed to mate with a corresponding castellated interface defined on an outer surface of the shaft 202 (FIG. 14). The castellated interface 1502 provides a zero clearance condition when the shaft 202 and the roll gear 1406 are pushed and mated together.

In some embodiments, the castellated interface 1502 may provide or otherwise define a self-locating feature 1504 that helps properly align the rolled gear 1406 with the shaft 202 (FIG. 14). In the illustrated embodiment, for example, the self-locating feature 1504 comprises a non-uniform castellation in the form of an elongated channel that exhibits an arcuate length that is larger than the other channels of the castellated interface 1502. In such embodiments, a corresponding non-uniform channel of the same arcuate length would be provided on the outer surface of the shaft 202 (FIG. 14) to mate with the non-uniform castellation. Consequently, with the self-locating feature 1504, the shaft 202 may be rotationally coupled to the roll gear 1406 in a single, predetermined angular orientation. This may prove advantageous in preventing excess "winding" of the drive cables 408a-d (FIGS. 4-5) within the shaft 202 during operation. More specifically, the shaft 202 may include a roll limiter 1408 engageable with interior features (not shown) provided by the roll gear 1406. The roll limiter 1408 has features (not shown) that are designed to interact with the drive housing 208 and thereby limit rotation of the shaft 202 to a predetermined angular rotation (e.g., 540°). The distal end of the roll limiter 1408 is keyed to the shaft 202, and if the roll gear 1406 is misassembled, the end effector 204 (FIGS. 2 and 4) will not be in the center of the roll range of the shaft 202.

Figure 16:
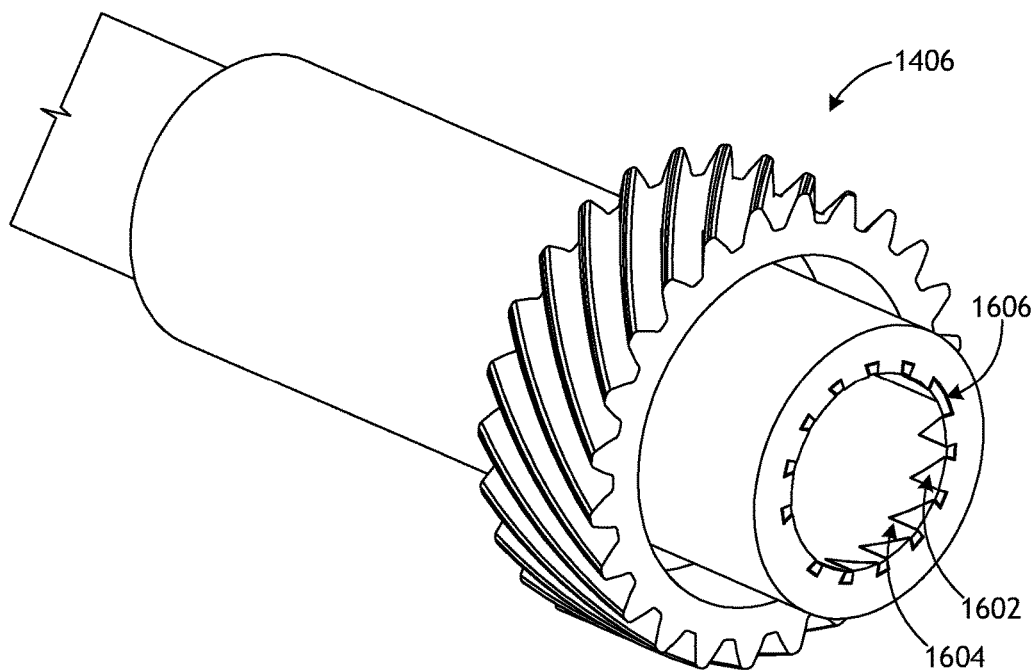
FIG. 16 is an isometric end view of another example of the roll gear of FIG. 14, according to one or more additional embodiments.

FIG. 16 is an isometric end view of another example of the roll gear 1406, according to one or more embodiments. In the illustrated embodiment, a castellated interface 1602 is defined on an inner surface of the roll gear 1406 and designed to mate with a corresponding castellated interface 1604 defined on an outer surface of the shaft 202. The shaft 202 may be held in contact with the roll gear 1406 due to an axial load applied by tension in the drive cables 408a-d (FIGS. 4-5) that is constantly in the device. Mating of the castellated interfaces 1602, 1604 provides a zero clearance condition when the shaft 202 and the roll gear 1406 are mated and otherwise pushed together.

In the illustrated embodiment, the castellated interfaces 1602, 1604 comprise matable angled features defined on both the roll gear 1406 and the shaft 202. In some embodiments, as illustrated, the castellated interface 1602 of the roll gear 1406 includes seven angled or triangular "teeth" that are mirrored down the center plane of the component. These teeth interface with mating angled or triangular cutouts provided by the shaft 202 to transmit the torque required to rotate the shaft 202. The castellated teeth mirrored about the center-line allow for shaft 202 rotation without any backlash or dead motion, and further allow for centering in one direction, while maintaining contact on the flat side (due to high tension in drive cables 408a-d of FIGS. 4-5) to provide efficient rotation and motion feedback. While seven teeth are depicted in the illustrated embodiment, more or less than seven may be employed, without departing from the scope of the disclosure.

In some embodiments, the castellated interfaces 1602, 1604 may provide or otherwise define a self-locating feature 1606 that helps properly align the rolled gear 1406 with the shaft 202. In the illustrated embodiment, for example, the self-locating feature 1606 comprises an angled castellation and corresponding cutout that are different from the remaining features of the castellated interfaces 1602, 1604. Consequently, the shaft 202 may be rotationally coupled to the roll gear 1406 in a single, predetermined angular orientation.

Cammed Articulation Joints and De-Articulation

Referring again briefly to FIG. 2, the surgical tool 200 may be used in a variety of types of laparoscopic surgery. In such embodiments, an incision is formed in the abdomen of a patient and a trocar (not shown) is inserted through the incision to form a pathway that provides access to the abdominal cavity. The shaft 202 may then be introduced into the abdominal cavity through the trocar and the end effector 204 may be subsequently operated to engage and/or treat tissue in a number of ways to achieve a diagnostic or therapeutic effect. During operation, the wrist 206 may be actuated to articulate the orientation of the end effector 204 away from the longitudinal axis $A_1$. Due to the joint stiffness at the wrist 206, however, the force required to manually remove the shaft 202 through the trocar when the end effector 204 is articulated can be high. Workflow may require users to remove the surgical tool 202 to clean the end effector 204 during the procedure, which makes removing the surgical tool 202 multiple times strenuous for the user.

Figure 17:
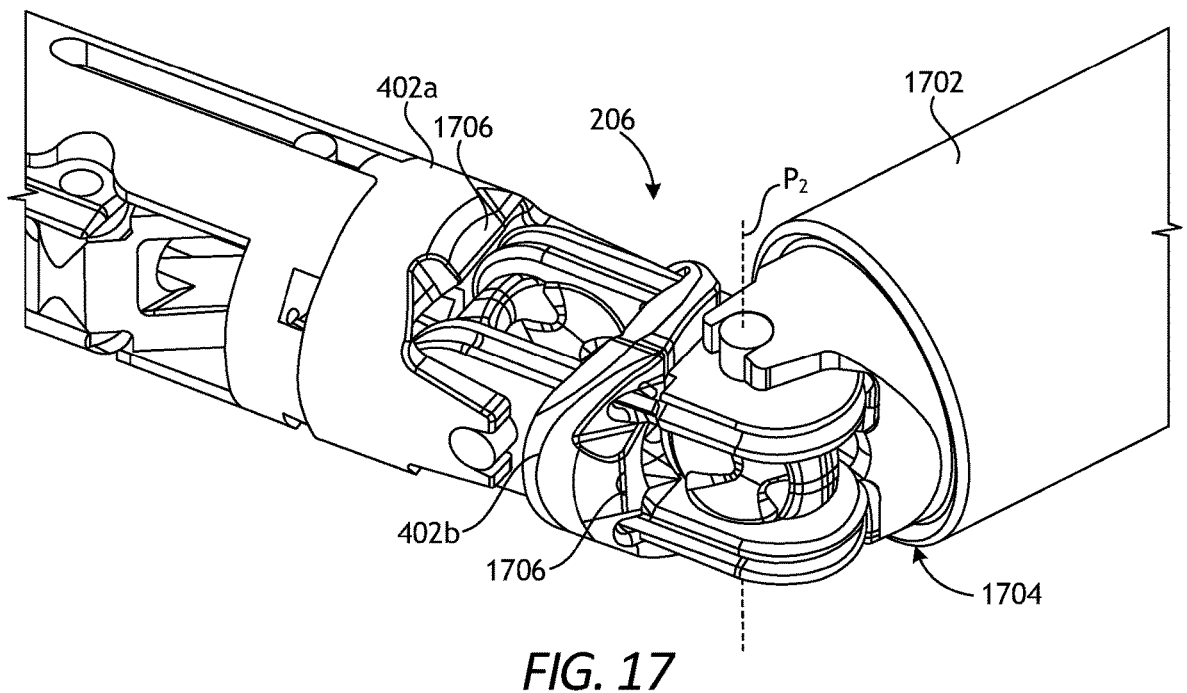
FIG. 17 is an enlarged isometric side view of the wrist of FIG. 2 extended through an example trocar, according to one or more embodiments.

FIG. 17 is an enlarged isometric side view of the wrist 206 extended through a trocar 1702, according to one or more embodiments. As illustrated, the wrist 206 extends past a distal end 1704 of the trocar 1702 and is articulated at the second pivot axis $P_2$. During an operation, if the user wishes to remove the surgical tool 200 (FIG. 2) from the trocar 1702, the user must decouple the surgical tool 200 from the tool driver and manually pull the surgical tool 200 from the trocar 1702. If the wrist 206 is in an articulated orientation, as depicted, a removal force exerted on the proximal end of the surgical tool 200 forces the wrist 206 and the end effector 204 (FIG. 2) against the distal end 1704 of the trocar 1702 to straighten the wrist 206. Conventional surgical tools and wrist joints require high forces to straighten the wrist, and exhibit force spikes and instances of the wrist catching on the trocar 1702 upon attempting to extract the surgical tool from the trocar 1702. This typically occurs at smaller articulation angles (e.g., between 15° and 30°) of the wrist 206 because the point of contact with the distal end 1704 of the trocar 1702 changes (e.g., shortening the moment arm).

According to embodiments of the present disclosure, the wrist 206 may include one or more camming features 1706 (two visible) that maintain contact with the distal end 1704 of the trocar 1702 during tool extraction. More specifically, the camming features 1706 may comprise contact surfaces provided or otherwise defined on the distal and intermediate linkages 402a,b and may allow for the contact surface where the distal end 1704 of the trocar 1702 engages the wrist 206 to change during tool extraction. The camming features 1706 help maintain a constant contact surface with the distal end 1704 of the trocar 1702 and therefore a constant moment arm to force the wrist 206 joint back to 0° articulation. Consequently, the camming features 1706 increase the moment arm (and thus mechanical advantage) and therefore decrease the force to remove at lower articulation angles.

Figure 18A:
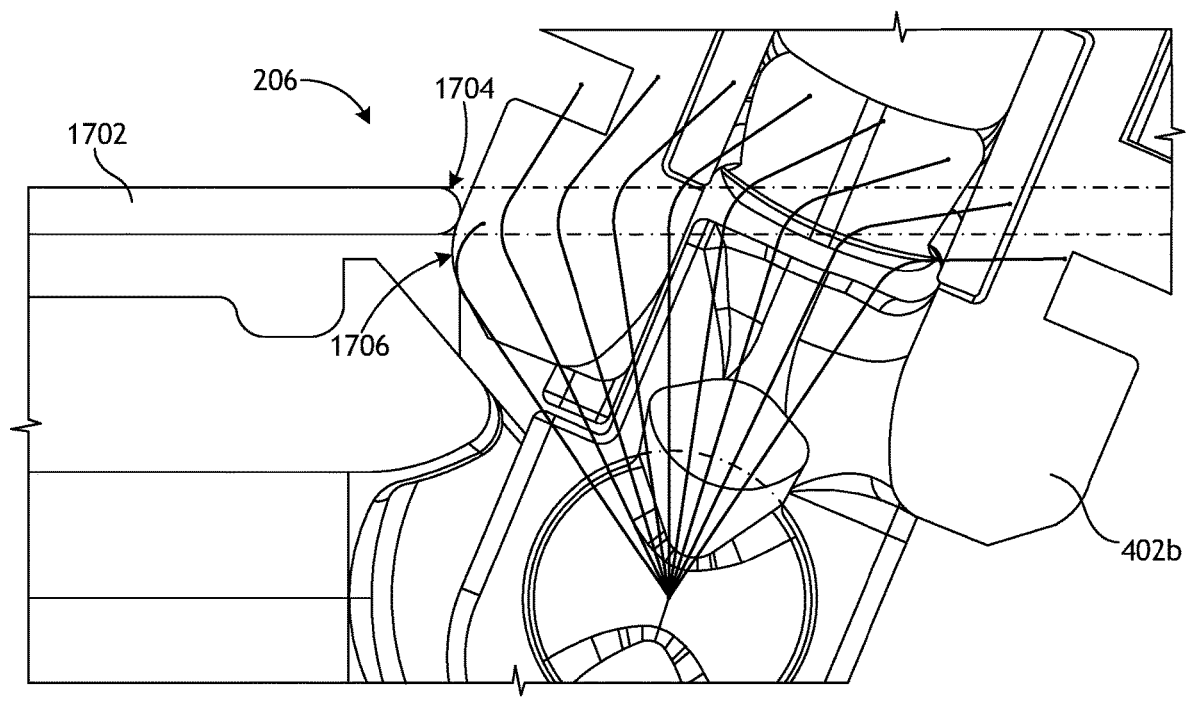
FIG. 18A is an enlarged side view of one embodiment of the wrist of FIG. 17, according to one or more embodiments.

FIG. 18A is an enlarged side view of one embodiment of the wrist 206, according to one or more embodiments. In the illustrated embodiment, the intermediate linkage 402b is in an articulated orientation and the distal end 1704 of the trocar 1702 is in contact with the intermediate linkage 402b in an attempt to remove the surgical tool 200 (FIG. 2) from the trocar 1702. As illustrated, the distal end 1704 of the trocar 1702 may contact the camming feature(s) 1706 during extraction; i.e., pulling the wrist to the left in FIG. 18A relative to the trocar 1702. The depicted design can result in a force spike at very high articulation angles (e.g., between 45° and 70°) due to an axial load being applied above the centerline of the cam. Nevertheless, the depicted design may demonstrate a reduction in the force spike at low articulation angles as compared to conventional wrist designs.

Figure 18B:
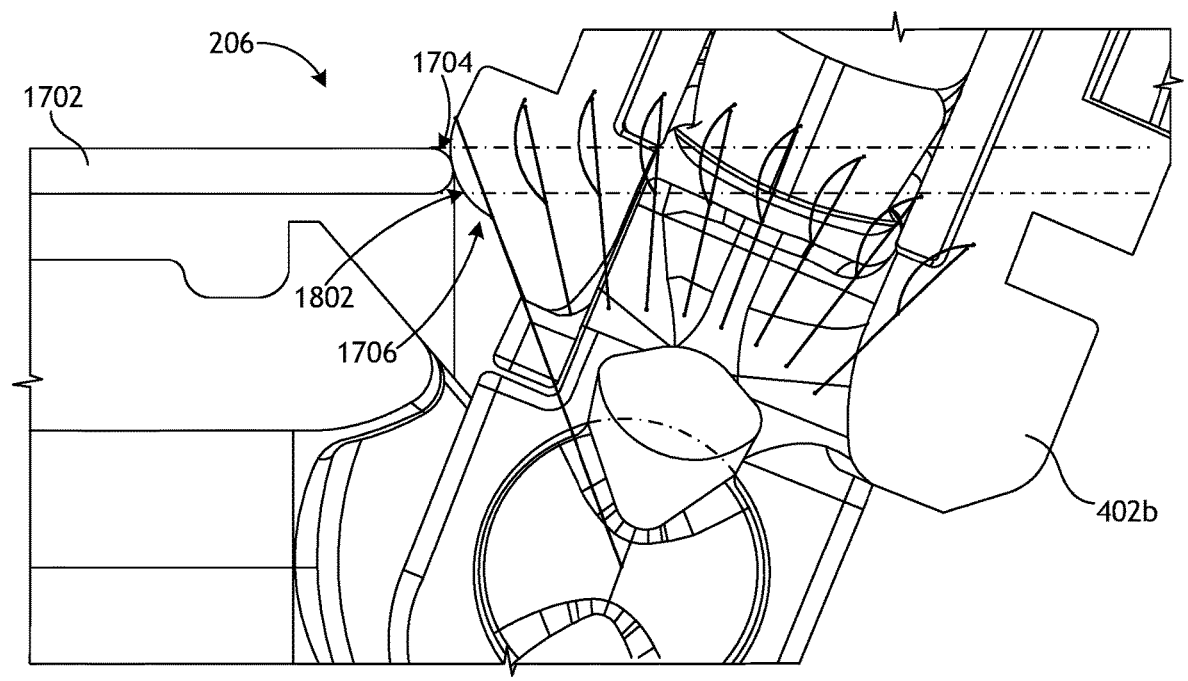
FIG. 18B is an enlarged side view of another embodiment of the wrist of FIG. 17, according to one or more additional embodiments.

FIG. 18B is an enlarged side view of another embodiment of the wrist 206, according to one or more additional embodiments. In the illustrated embodiment, the intermediate linkage 402b is again in an articulated orientation and the distal end 1704 of the trocar 1702 is in contact with the intermediate linkage 402b in an attempt to remove the surgical tool 200 (FIG. 2) from the trocar 1702 i.e., pulling the wrist to the left in FIG. 18B relative to the trocar 1702.

As illustrated, the distal end 1704 of the trocar 1702 may contact the camming feature(s) 1706 during extraction. In the illustrated embodiment, however, the camming feature (s) 1706 may provide or otherwise define a rounded protuberance 1802 engageable with the distal end 1704 of the trocar 1702. The rounded protuberance 1802 may act as a cam surface that contacts the distal end 1704 of the trocar 1702 and may provide a much better moment arm for the trocar 1702 from the centerline of the camming feature(s) 1706. More specifically, at high articulation angles (e.g., between 45° and 70°), the trocar loading on the wrist 206 may be below the radius center of the protuberance(s) 1802, which enables rotation (reorientation) of the wrist 206 without experiencing a load (force) spike. In the depicted design, the distal end 1704 of the trocar 1702 always contacts above the centerline of the protuberance(s) 1802, which effectively removes the potential for the distal end 1704 to catch on any portion of the wrist 206.

External Connector for Surgical Tool Tailpiece

Figure 19:
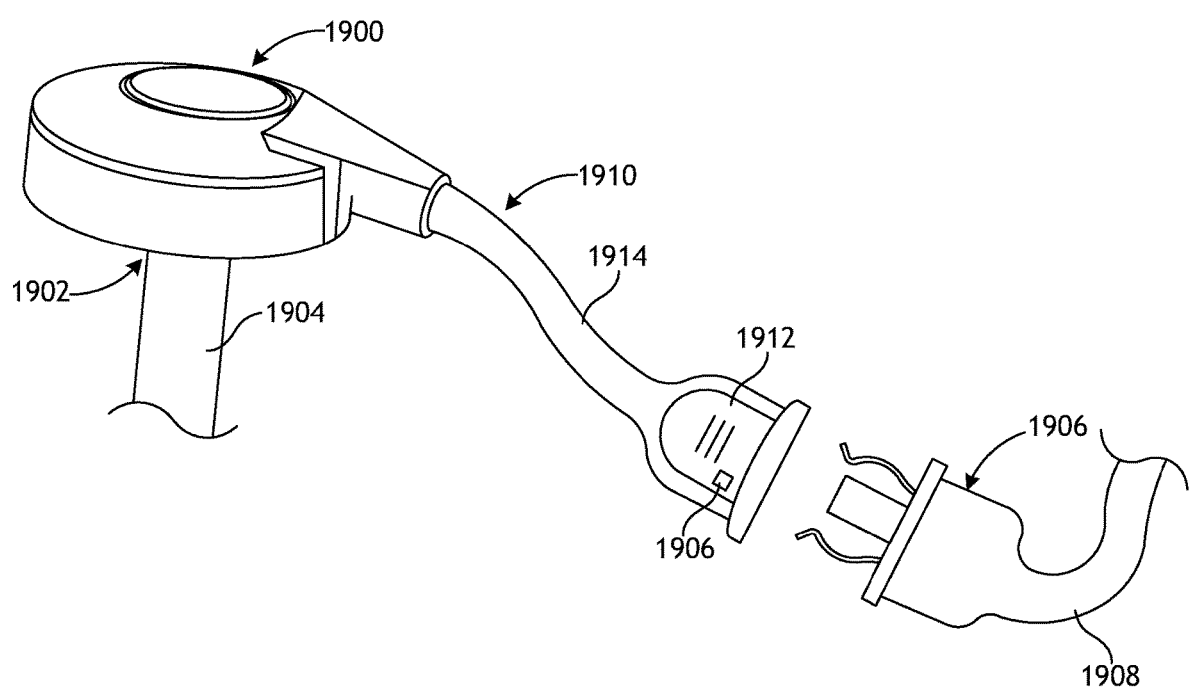
FIG. 19 is a schematic view of an example tailpiece for a surgical tool, according to one or more embodiments.

FIG. 19 is a schematic view of an example tailpiece 1900 for an example surgical tool 1902, according to one or more embodiments. In some embodiments, the surgical tool 1902 may be the same as or similar to the surgical tool 200 of FIG. 2, but the tailpiece 1900 may alternatively form part of any other type of robotic surgical tool or instrument. The tailpiece 1900 is typically located at the most proximal portion of the shaft 1904 of the surgical tool 1902, and the drive cables (not shown) that operate the surgical tool 1902 may terminate in the tailpiece 1900. In some embodiments, various tensioning mechanisms (not shown) may be housed within the tail piece 1900 to create and maintain tension in the antagonistic drive cables during operation.

In embodiments where the surgical tool 1902 is also designed to provide electrical current to an end effector for electrocautery purposes or the like, the tailpiece 1900 may also house an electrical connector and a female electrical receptacle. An adapter 1906 from a single use cable 1908 extending from a generator (not shown) may be configured to mate with the female receptacle and thereby provide electrical power to the surgical tool 1902. A conductor (not shown) may extend from the electrical connector to an end effector. The conductor may extend parallel with the shaft 1904, either within the shaft 1904 or in a counter-bored hole or channel defined in the shaft 1904.

A smaller and lighter tailpiece 1900 may be advantageous in providing effective and more efficient operation of the surgical tool 1902. According to embodiments of the disclosure, one way to make the tailpiece 1900 smaller and lighter is to move the electrical connector out of the tailpiece 1900. More specifically, as illustrated, the surgical tool 1902 may include an electrical connector 1910 extending from the tailpiece 1900 and terminating at a female receptacle 1912 configured to receive and be coupled to the adapter 1906. Accordingly, the electrical connector 1910 is located outside of the constraints of the tailpiece, which would result in the tailpiece 1900 only housing the tensioner mechanisms for the drive cables. The electrical connector 1910 may be designed for single use or may be reusable after proper sterilization or autoclaving.

In some embodiments, the electrical connector 1910 may include a pigtail cord 1914, which may be overmolded with silicone or another non-conductive material. The cord 1914 may exhibit a length ranging between about two inches and about five inches, but could alternatively exhibit a length greater than five inches, without departing from the scope of the disclosure.

In some embodiments, the female receptacle may include or otherwise house a programmable read-only memory (ROM) device or chip 1916. In at least one embodiment, the chip 1916 may comprise an erasable programmable read-only memory (EPROM) chip. The chip 1916 may be configured to provide a tool identifier that remains with the surgical tool 1902. In some embodiments, the chip 1916 may house code that defines the instrument product code.

Embodiments disclosed herein include:

A. A surgical tool includes a drive housing with an elongate shaft extending therefrom and an end effector arranged at a distal end of the shaft, a drive input rotatably mounted to the drive housing and an input shaft extending from the drive input, upper and lower capstans mounted to the input shaft, first and second drive cables coupled to the upper and lower capstans, respectively, and extending to the end effector, and a clutch feature arranged to mate the upper capstan to the lower capstan and movable between an engaged position, where rotation of the input shaft in either angular direction rotates the upper and lower capstans in the same angular direction, and a disengaged position, where the upper and lower capstans are rotatable independent of each other in at least one angular direction.

B. A method of pre-tensioning a surgical tool includes providing a surgical tool that includes a drive housing with an elongate shaft extending therefrom and an end effector arranged at a distal end of the shaft, a drive input rotatably mounted to the drive housing with an input shaft extending from the drive input, upper and lower capstans mounted to the input shaft, first and second drive cables coupled to the upper and lower capstans, respectively, and extending to the end effector. The method further includes rotating one or both of the upper and lower capstans relative to the other of the upper and lower capstans and thereby increasing tension in one or both of the first and second drive cables, and mating the upper and lower capstans at a clutch feature such that rotation of the input shaft in either angular direction correspondingly rotates the upper and lower capstans simultaneously in the same angular direction.

C. A drive assembly for a surgical tool includes an input shaft extending from a drive input rotatably mounted to a drive housing of the surgical tool, upper and lower capstans mounted to the input shaft, first and second drive cables coupled to the upper and lower capstans, respectively, and extendable to an end effector of the surgical tool, and a clutch feature arranged to mate the upper and lower capstans and movable between an engaged position, where rotation of the input shaft in either angular direction correspondingly rotates the upper and lower capstans in the same angular direction, and a disengaged position, where the upper and lower capstans are rotatable independent of each other in at least one angular direction.

Each of embodiments A, B, and C may have one or more of the following additional elements in any combination: Element 1: further comprising a setting feature that locks the clutch feature in the engaged position and thereby prevents axial separation of the upper and lower capstans. Element 2: wherein the setting feature comprises a pin extendable through an aperture defined in the upper capstan and engageable with a recess defined in the input shaft. Element 3: wherein the clutch feature comprises a plurality of ratchet teeth defined on both capstans. Element 4: wherein the plurality of ratchet teeth allow the upper and lower capstans to rotate relative to each other in opposite angular directions when the clutch feature is in the disengaged position, and wherein the plurality of ratchet teeth are interlocked and couple the upper and lower capstans for simultaneous rotation in the either angular direction when the clutch feature is in the engaged position. Element 5: wherein the clutch feature comprises matable geometric features defined on both capstans. Element 6: wherein the matable geometric features comprise a drive protrusion defined on one of the upper or lower capstans, and a drive pocket defined on the other of the upper and lower capstans and sized to receive the drive protrusion. Element 7: wherein rotating one of the upper or lower capstans relative to the other of the upper and lower capstans applies tension in one or both of the first and second drive cables. Element 8: wherein rotating the upper and lower capstans in opposite angular directions applies tension in the first and second drive cables.

Element 9: further comprising locking the clutch feature in an engaged position with a setting feature and thereby preventing axial separation of the upper and lower capstans. Element 10: wherein the setting feature comprises a pin and locking the clutch feature in the engaged position comprises extending the pin through an aperture defined in the upper capstan, and receiving a portion of the pin in a recess defined in the input shaft. Element 11: wherein the clutch feature comprises a plurality of ratchet teeth defined on both capstans, and wherein rotating one or both of the upper and lower capstans relative to the other of the upper and lower capstans comprises ratcheting the upper and lower capstans relative to each other in opposite angular directions. Element 12: further comprising interlocking the plurality of ratchet teeth defined on both capstans, and maintaining a set tension on the first and second drive cables when the plurality of ratchet teeth defined on both capstans are interlocked. Element 13: wherein the clutch feature comprises matable geometric features defined on both capstans, and wherein mating the upper and lower capstans at the clutch feature comprises receiving a drive protrusion defined on one of the upper or lower capstans within a drive pocket defined on the other of the upper and lower capstans. Element 14: wherein rotating one or both of the upper and lower capstans relative to the other of the upper and lower capstans comprises rotating the upper and lower capstans simultaneously in opposite angular directions.

Element 15: further comprising a setting feature that locks the clutch feature in the engaged position and thereby prevents axial separation of the upper and lower capstans. Element 16: wherein the clutch feature comprises a plurality of ratchet teeth defined on both capstans. Element 17: wherein the clutch feature comprises matable geometric features defined on both capstans.

By way of non-limiting example, exemplary combinations applicable to A, B, and C include: Element 1 with Element 2; Element 3 with Element 4; Element 5 with Element 6; Element 9 with Element 10; and Element 11 with Element 12.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing with an elongate shaft extending therefrom and an end effector arranged at a distal end of the elongate shaft;
   a drive input rotatably mounted to the drive housing and an input shaft extending from the drive input, the input shaft defining a rotational axis;
   upper and lower capstans mounted to the input shaft;
   first and second drive cables coupled to the upper and lower capstans, respectively, and extending to the end effector; and
   a clutch feature including a plurality of ratchet teeth on at least a first one of the upper and lower capstans, each of the ratchet teeth being radially asymmetrically shaped about the rotational axis and arranged to selectively mate with at least one tooth on a second one of the upper and lower capstans to permit the upper capstan and the lower capstan to rotate with respect to one another in at least one angular direction about the rotational axis, the clutch feature movable between an engaged position, where rotation of the input shaft in either angular direction rotates the upper and lower capstans in the same angular direction, and a disengaged position, where the upper and lower capstans are rotatable independent of each other in the at least one angular direction.

2. The surgical tool of claim 1, further comprising a setting feature that locks the clutch feature in the engaged position and thereby prevents axial separation of the upper and lower capstans.

3. The surgical tool of claim 2, wherein the setting feature comprises a pin extendable through an aperture defined in the upper capstan and engageable with a recess defined in the input shaft.

4. The surgical tool of claim 1, wherein the at least one tooth comprises a plurality of ratchet teeth such that the clutch feature comprises a plurality of ratchet teeth defined on both capstans.

5. The surgical tool of claim 4, wherein the plurality of ratchet teeth allow the upper and lower capstans to rotate relative to each other in opposite angular directions when the clutch feature is in the disengaged position, and
   wherein the plurality of ratchet teeth are interlocked and couple the upper and lower capstans for simultaneous rotation in the either angular direction when the clutch feature is in the engaged position.

6. The surgical tool of claim 1, wherein the clutch feature comprises matable geometric features defined on both capstans.

7. The surgical tool of claim 6, wherein the matable geometric features comprise a drive protrusion defined on one of the upper or lower capstans, and a drive pocket defined on the other of the upper and lower capstans and sized to receive the drive protrusion.

8. The surgical tool of claim 1, wherein rotating one of the upper or lower capstans relative to the other of the upper and lower capstans applies tension in one or both of the first and second drive cables.

9. The surgical tool of claim 1, wherein rotating the upper and lower capstans in opposite angular directions applies tension in the first and second drive cables.

10. A drive assembly for a surgical tool, comprising:
    an input shaft extending from a drive input rotatably mounted to a drive housing of the surgical tool;
    upper and lower capstans mounted to the input shaft, the input shaft defining a rotational axis;
    first and second drive cables coupled to the upper and lower capstans, respectively, and extendable to an end effector of the surgical tool; and
    a clutch feature including a plurality of ratchet teeth on at least a first one of the upper and lower capstans, each of the ratchet teeth radially asymmetrically shaped about the rotational axis and arranged to selectively mate with at least one tooth on a second one of the upper and lower capstans to permit the upper and lower capstans to rotate with respect to one another in at least one angular direction about the rotational axis, the clutch feature movable between an engaged position, where rotation of the input shaft in either angular direction correspondingly rotates the upper and lower capstans in the same angular direction, and a disengaged position, where the upper and lower capstans are rotatable independent of each other in the at least one angular direction.

11. The drive assembly of claim 10, further comprising a setting feature that locks the clutch feature in the engaged position and thereby prevents axial separation of the upper and lower capstans.

12. The drive assembly of claim 10 wherein the clutch feature comprises a plurality of ratchet teeth defined on both capstans.

13. The drive assembly of claim 10, wherein the clutch feature comprises matable geometric features defined on both capstans.

* * * * *